(12) United States Patent
Tasch et al.

(10) Patent No.: US 6,916,295 B2
(45) Date of Patent: Jul. 12, 2005

(54) METHOD AND SYSTEM FOR DYNAMIC RECORDATION AND ANALYSIS OF ANIMAL CHARACTERISTICS

(75) Inventors: Uri Tasch, Baltimore, MD (US); Parimal Rajkondawar, Madison, WI (US)

(73) Assignee: University of Maryland, Baltimore County, Baltimore, MD (US)

(*) Notice: Subject to any disclaimer, the term of this patent is extended or adjusted under 35 U.S.C. 154(b) by 69 days.

(21) Appl. No.: 10/743,306

(22) Filed: Dec. 23, 2003

(65) Prior Publication Data

US 2004/0199089 A1 Oct. 7, 2004

Related U.S. Application Data

(60) Provisional application No. 60/473,886, filed on May 29, 2003, and provisional application No. 60/435,320, filed on Dec. 23, 2002.

(51) Int. Cl.[7] .......................... A61B 5/103; A61B 5/117
(52) U.S. Cl. ..................................................... 600/595
(58) Field of Search ................................ 600/595, 592, 600/587

(56) References Cited

U.S. PATENT DOCUMENTS

| 4,195,643 A | 4/1980 | Pratt, Jr. |
| 6,183,425 B1 | 2/2001 | Whalen et al. |

*Primary Examiner*—Max F. Hindenburg
*Assistant Examiner*—Brian Szmal
(74) *Attorney, Agent, or Firm*—McDermott Will & Emery LLP

(57) ABSTRACT

A method and instruction set stored in a computer readable medium are provided to singulate the limbs of a plurality of animals traversing an instrumented force-sensing floor. The method and the instruction set include the steps of (a) obtaining a data file comprising positional data and ground reaction force data for the animals traversing an instrumented force-sensing floor; (b) dividing the positional data into a plurality of time zones, each time zone having a start time and an end time; (c) determining whether each of said time zones represents positional data and ground reaction force data for a single limb or for multiple limbs; (d) singulating multiple limb time zones into a plurality of separate single limb time zones; (e) identifying each limb in each time zone as a fore limb or a hind limb and a left limb or a right limb; and (f) associating each identified fore and hind limb with a respective one of the animals.

60 Claims, 21 Drawing Sheets

Table 1. A sample of an YYMMDDxxx.ID file

| Time | File running number YYMMDDxxx | Cow's Transponder | Cow's Number | Number of cows per file ($n$) |
|---|---|---|---|---|
| 14:24:18 | 020527020 | 18276 | 199 | 2 |
| 14:24:18 | 020527020 | 17112 | 1027 | |
| 14:28:13 | 020527021 | 17212 | 961 | 4 |
| 14:28:13 | 020527021 | 17225 | 217 | |
| 14:28:13 | 020527021 | 18231 | 980 | |
| 14:28:13 | 020527021 | 15293 | 1026 | |
| 14:33:18 | 020527022 | 20756 | 991 | 3 |
| 14:33:18 | 020527022 | 23221 | 213 | |
| 14:33:18 | 020527022 | 25260 | 885 | |

*Figure 2*

Table 3. Definitions of the statistical parameters evaluated in each TimeZone. The parameters are based on Y position and GRF values.

| LimbZoneStatistics | Description |
| --- | --- |
| Yave | Average value of Y position |
| Ymax | Maximum value of Y position |
| Ymin | Minimum value of Y position |
| YSLOPEmax | Maximum Y position slope |
| tYSLOPEmax | Time at which maximum Y position slope occurs |
| YSLOPEmin | Minimum Y position slope |
| tYSLOPEmin | Time at which minimum Y position slope occurs |
| PGRF | Peak Ground Reaction Force |
| AGRF | Average Ground Reaction Force |
| GRF_pos_SLOPE | Counter of positive GRF slopes |
| GRF_neg_SLOPE | Counter of negative GRF slopes |
| Delta_GRF_SLOPE | The number of times GRF changes its slope from positive to negative |
| J_Limb | Number of limbs in a time zone |

*Figure 5*

Table 3. Numerical values of LimbZoneStatistics for the data plots shown in Figure 4. TimeZone_1 reflects a single limb (J_Limb = 1), TimeZone_2 reflects 2 limbs (J_Limb = 2), and TimeZone_3 reflects 3 limbs (J_Limb =3)

| LimbZoneStatistics file 020527020 | TimeZone_1 | TimeZone_2 | TimeZone_3 |
|---|---|---|---|
| Yave | 54.58 | 45.99 | 56.40 |
| Ymax | 55.05 | 59.10 | 71.91 |
| Ymin | 53.99 | 30.96 | 25.49 |
| YSLOPEmax | 0.98 | 2.10 | 14.28 |
| tYSLOPEmax | 2.54 | 3.82 | 4.97 |
| YSLOPEmin | -0.36 | -28.03 | -10.56 |
| tYSLOPEmin | 2.18 | 3.72 | 6.23 |
| PGRF | 0.42 | 0.46 | 0.75 |
| AGRF | 0.36 | 0.32 | 0.46 |
| GRF_pos_SLOPE | 0 | 1 | 73 |
| GRF_neg_SLOPE | 0 | 14 | 26 |
| DeltaGRF_SLOPE | 3 | 7 | 9 |
| J_Limb | 1 | 2 | 3 |
| LimbSequence | F | - | - |

*Figure 6*

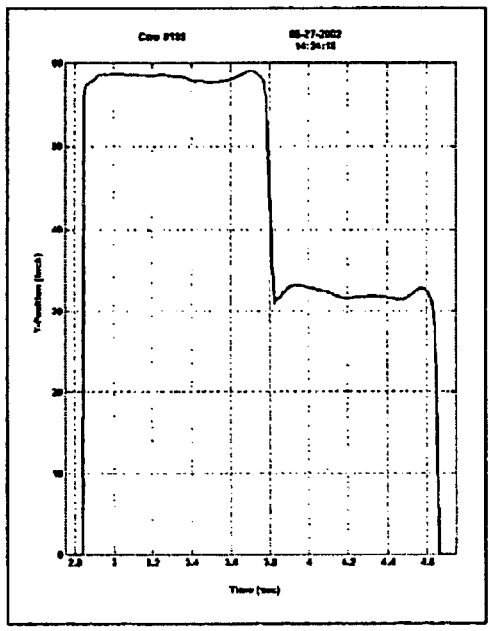
*Figure 7(a)*
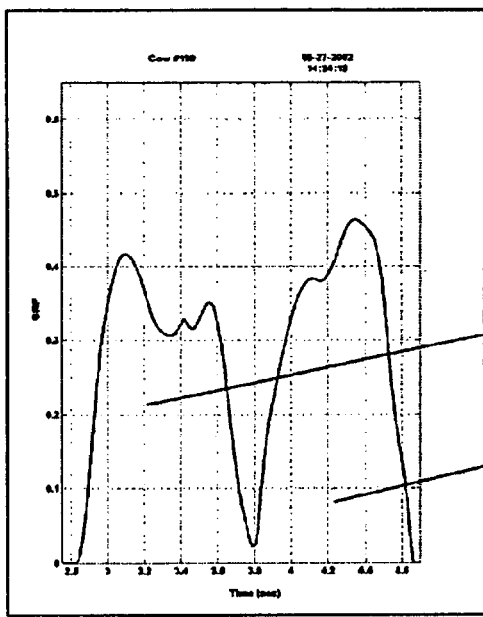 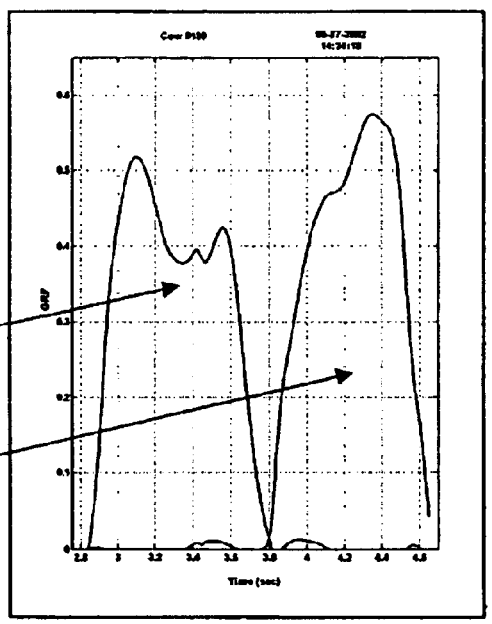
*Figure 7(b)*   *Figure 7(c)*

| LimbZoneStatistics for file 020527020 (n=2) | 1st Animal Cow 199 | | (n-1) animals Cow 1027 | |
|---|---|---|---|---|
| | Time Zone_1 | Time Zone_21 | Time Zone_22 | Time Zone_3 |
| Yave | 54.58 | 58.40 | 32.14 | 56.40 |
| Ymax | 55.05 | 58.40 | 32.14 | 71.91 |
| Ymin | 53.99 | 58.40 | 32.14 | 25.49 |
| YSLOPEmax | 0.98 | 0.73 | 1.01 | 14.28 |
| tYSLOPEmax | 2.54 | 3.55 | 4.45 | 4.97 |
| YSLOPEmin | -0.36 | -0.63 | -0.82 | -10.56 |
| tYSLOPEmin | 2.18 | 3.32 | 4.06 | 6.23 |
| PGRF | 0.42 | 0.42 | 0.47 | 0.75 |
| AGRF | 0.36 | 0.35 | 0.39 | 0.46 |
| GRF_pos_SLOPE | 0 | 0 | 0 | 73 |
| GRF_neg_SLOPE | 0 | 0 | 0 | 26 |
| DeltaGRF_SLOPE | 3 | 5 | 1 | 9 |
| J_Limb | 1 | 1 | 1 | 3 |
| LimbSequence | F | H | F | - |

Table 4: TimeZone_2 (Table 3) is a two limb zone (J_Limb=2) and the TwoLimbSeparation function is called to convert TimeZone2 into TimeZone_21 and 22. The limb zone statistics are calculated for the two separated time zones and the LimbSequence

*Figure 8*

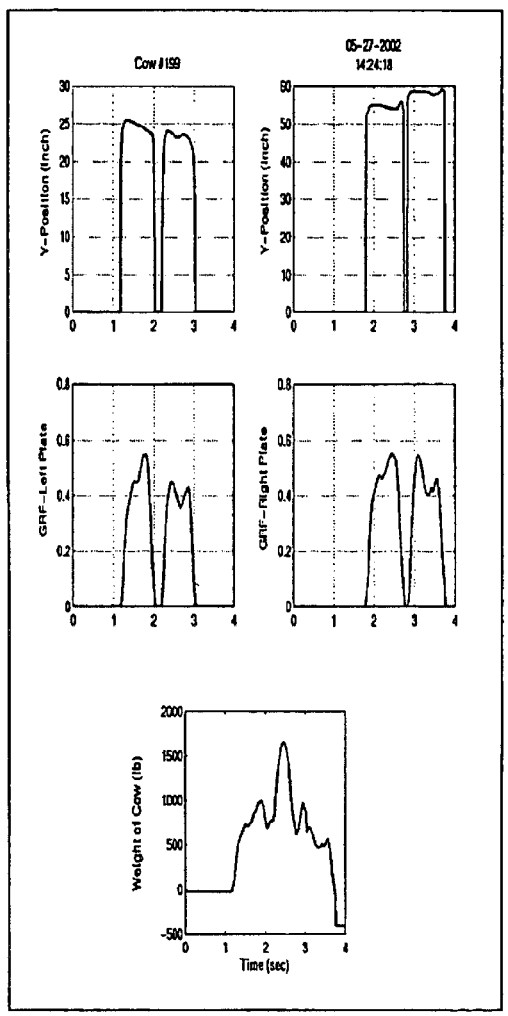 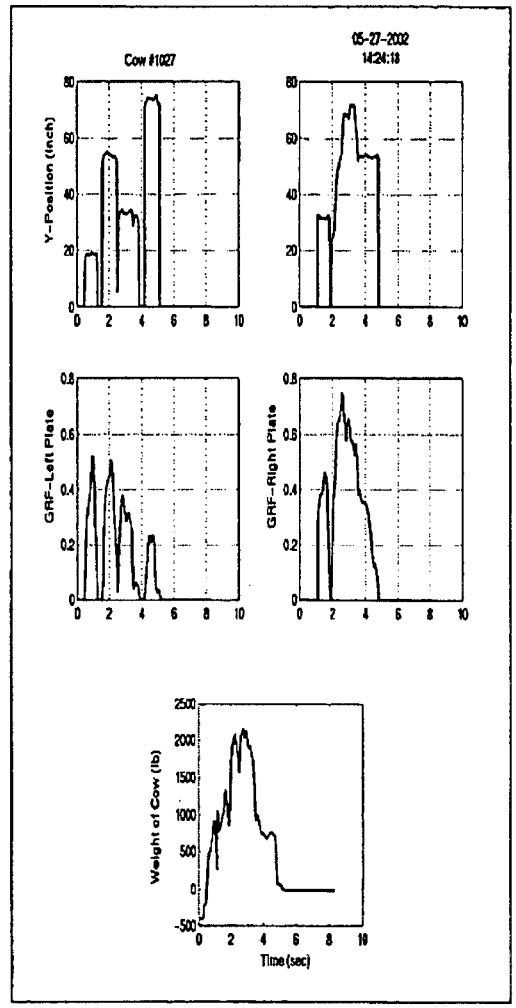
*Figure 9(a)*  *Figure 9(b)*

METHOD AND SYSTEM FOR DYNAMIC RECORDATION AND ANALYSIS OF ANIMAL CHARACTERISTICS

RELATED APPLICATIONS

This application claims priority from U.S. Provisional Application Nos. 60/473,886 filed on May 29, 2003, and 60/435,320 filed on Dec. 23, 2002.

This application is generally related to, but does not claim priority from, U.S. patent application Ser. No. 09/827,311, incorporated herein by reference.

BACKGROUND INFORMATION

The present disclosure relates to a new method and system for dynamic recordation and analysis of animal characteristics including, but not limited to, an animal's weight or an animals biomechanic or biometric data (e.g., limb displacements, velocities, accelerations, and/or forces during one or more activities (e.g., standing, walking, trotting, etc.)) from the measured data, whether directly or by derivation, and analysis thereof. The dynamic recordation and analysis permits determination of characteristics of interest for animals, particularly four legged animals, including but not limited herd-animals such as dairy cows, non-dairy cows, pigs, and sheep.

Dairy production is an important industry in the U.S. and a major branch of agriculture in many countries around the world. Cow lameness caused by hoof and leg ailments is a costly problem for the dairy farmer. Lameness necessitates medical treatment, reduces milk production, results in decreased body condition, impairs reproduction performance, and adversely impacts the social status of animals. Economically, lameness is reported to be the third most costly problem for dairy herds following mastitis and sub-fertility. The average cost of lameness is reported to be 412 dollars per incident and the annual incidence rate in the U.S. is fifteen percent. Thus, the annual economic losses due to lameness is over 570 million dollars for the over nine million U.S. cows. These losses significantly impair dairy farms and harm the entire bovine industry. Lameness in dairy herds is, accordingly, a critical economic factor and a vital animal-welfare issue for the dairy industry around the world.

Etiological factors contribute to lameness including nutrition, bacterial and fungal infections, bacterial endotoxin, environmental conditions, housing, flooring, feeding management, and cow behaviors. Prior to the development of a viable Reaction Force Detection (RFD) currently being commercialized by Bou-Matic, LLC of Madison, Wis., disclosed in "Method and Device for Analyzing Weight and Walking Gait", U.S. patent application Ser. No. 09/827,311, by the present invention and others, early detection of hoof and leg ailments comprised, in large part, visual observation of severe or latter stages of lameness by farmers. At such latter stages, even successful interventions are more expensive to address and are unable to return the cow, or other herd animal, back into circulation quickly, thus compounding the cost to the farmer. Thus, there existed a need in the art for a method and an apparatus able to provide early detection of hoof and leg problems, which will enable prompt veterinarian medical intervention to reduce economic losses, lessen the pain that the animal endures, and expedite the animal's recovery process. There also existed a need for an early detection system enabling scientific testing of management programs designed to reduce the rate of incidence of lameness in dairy herds.

However, despite the significant advances realized by the aforementioned Reaction Force Detection (RFD) and associated disclosure in the "Method and Device for Analyzing Weight and Walking Gait" U.S. patent application Ser. No. 09/827,311, a continuing need exists for improvements in the extraction of animal characteristics, including but not limited to data such as limb displacements, velocities, accelerations, and/or forces (e.g., biomechanic data) from the measured data, whether directly or by derivation, and analysis thereof.

Body weight is another animal characteristic that has become an effective management parameter for the dairy industry (Maltz, et al., 1997), and use of walkthrough scales (Peiper, et al., 1993) in moderate and large farms is increasing. When a dairy herd is walked through a stationary scale, the herd must be managed and singulated so as to permit the recordation of the weight of each individual animal. Since cattle is a herd-type animal, this singulation poses a management challenge that is currently addressed by two commercially available solutions: (i) pneumatically actuated entrance and exit gates and (ii) a passive S shape gate that is operated by the animals themselves, such as manufactured by S.A.E. Afikim of Israel (see, e.g., www.afimilk.co.il).

However, both of the weighing systems and the RFD system, utilize means to singulate the animals, thereby disrupting and slowing down the animal traffic and imposing extra work on the animal caretakers. Therefore, a need exists for a means by which animals may be singulated, for such purposes as weighing or force detection, with a lesser degree of disruption to animal traffic than presently imposed by current systems.

SUMMARY OF THE DISCLOSURE

The present disclosure relates to a new method and system for dynamic recordation and analysis of animal characteristics including, but not limited to, an animal's weight or an animals biomechanic or biometric data (e.g., limb displacements, velocities, accelerations, and/or forces during one or more activities (e.g., standing, walking, trotting, etc.)) from the measured data, whether directly or by derivation, and analysis thereof.

In one aspect, a method and computer readable instruction set are provided to singulate the limbs of a plurality of animals traversing an instrumented force-sensing floor. In such aspect, the method and the instruction set include the steps of (a) obtaining a data file comprising positional data and ground reaction force data for the animals traversing an instrumented force-sensing floor; (b) dividing the positional data into a plurality of time zones, each time zone having a start time and an end time; (c) determining whether each of said time zones represents positional data and ground reaction force data for a single limb or for multiple limbs; (d) singulating multiple limb time zones, such as by induction, into a plurality of separate single limb time zones; (e) identifying each limb in each time zone as a fore limb or a hind limb and a left limb or a right limb; and (f) associating each identified fore and hind limb with a respective one of the animals.

In accord therewith, there is provided herein a computer-based means by which animals may singulated through software, rather by physical impediments to animal traffic. In one aspect, the singulation is performed by induction. In other words, one cow at a time is separated from a group of n cows so we get one single cow and (n−1) cows in the resultant new group. This is iterative process that is repeated j times so every time we get one single cow and a group of (n−j) cows. This process is repeated until (n−j)=1. Singulation by induction enables separation of any number of cows that may go together across a detection plate system or detection field, which is limited only by hardware constraints (i.e., memory and CPU limitations).

The disclosed singulation technique records limb movement variables (LMVs) for a group of n cows that walk together through, for example, a RFD, into N files, each containing the LMVs of a single animal. Unlike the conventional physical singulation techniques, the disclosed singulation technique does not utilize barriers to restrict the measurement zone to only one animal at a time to ensure that a given cow's ($n_x$) data is assigned directly to a data file corresponding to such cow. Instead, the disclosed singulation technique relies upon software-based operations to determine whether or not one or more of the n animals are simultaneously present within the measurement zone and to extract the LMVs present in one of the data files (a subset of files which, for the purposes of the present example, contains a number of data files less than the number of animals n) into a number of separate files corresponding to the detected animals (e.g., $n_x$, $n_y$) simultaneously present within the measurement zone.

Additional advantages and other features of the present invention will be set forth in part in the description which follows and in part will become apparent to those having ordinary skill in the art upon examination of the following or may be learned from the practice of the invention. The advantages of the invention may be realized and obtained as particularly pointed out in the appended claims.

BRIEF DESCRIPTION OF THE FIGURES

FIG. 2 shows a table showing sample informational files useful in accord with the presently disclosed concepts.

FIG. 5 is a table with definitions of the statistical parameters evaluated for each TimeZone based upon Y-position and GRF values in accord with the present concepts.

FIG. 6 is a table showing numerical values of LimbZoneStatistics for the data plots in FIG. 4, wherein TimeZone_1 reflects a single limb, TimeZone_2 reflects limbs, and TimeZone_3 reflects three limbs, in accord with the present concepts.

FIGS. 7(a)–7(c) show singulation of two-limb TimeZone_2 of FIG. 6 in accord with the present concepts, wherein FIG. 7(a) is a Y-position plot, FIG. 7(b) is a GRF plot, and FIG. 7(c) is the GRF plot of FIG. 7(b) following singulation using a TwoLimbSeparation function in accord with the present concepts.

FIG. 8 shows, for the example of FIG. 6 (Table 3) wherein TimeZone_2 is a two limb zone, application of the TwoLimbSeparation function to convert TimeZone_2 into two separate time zones TimeZone_21 and TimeZone_22, calculation of limb zone statistics for the separated time zones, and assignment of LimbSequence in accord with the present concepts.

FIGS. 9(a)–9(b) respectively show Y-position, GRF, and body weight plots for the separated or singulated records for the aforementioned cows 199 and 1027 in accord with the present concepts.

FIGS. 11(a)–(d) generally show separation of the records of three cows (991, 213, and 885) into three records having a single cow in each, wherein FIG. 11(a) is the records of three cows and FIGS. 11(b)–(d) respectively show Y-position, GRF, and weight plots of individual cows 991, 213, and 885.

FIG. 12 generally show separation of the records of four cows (961, 217, 980 and 1026) into four records having a single cow in each, wherein

DETAILED DESCRIPTION

Figure 1A:
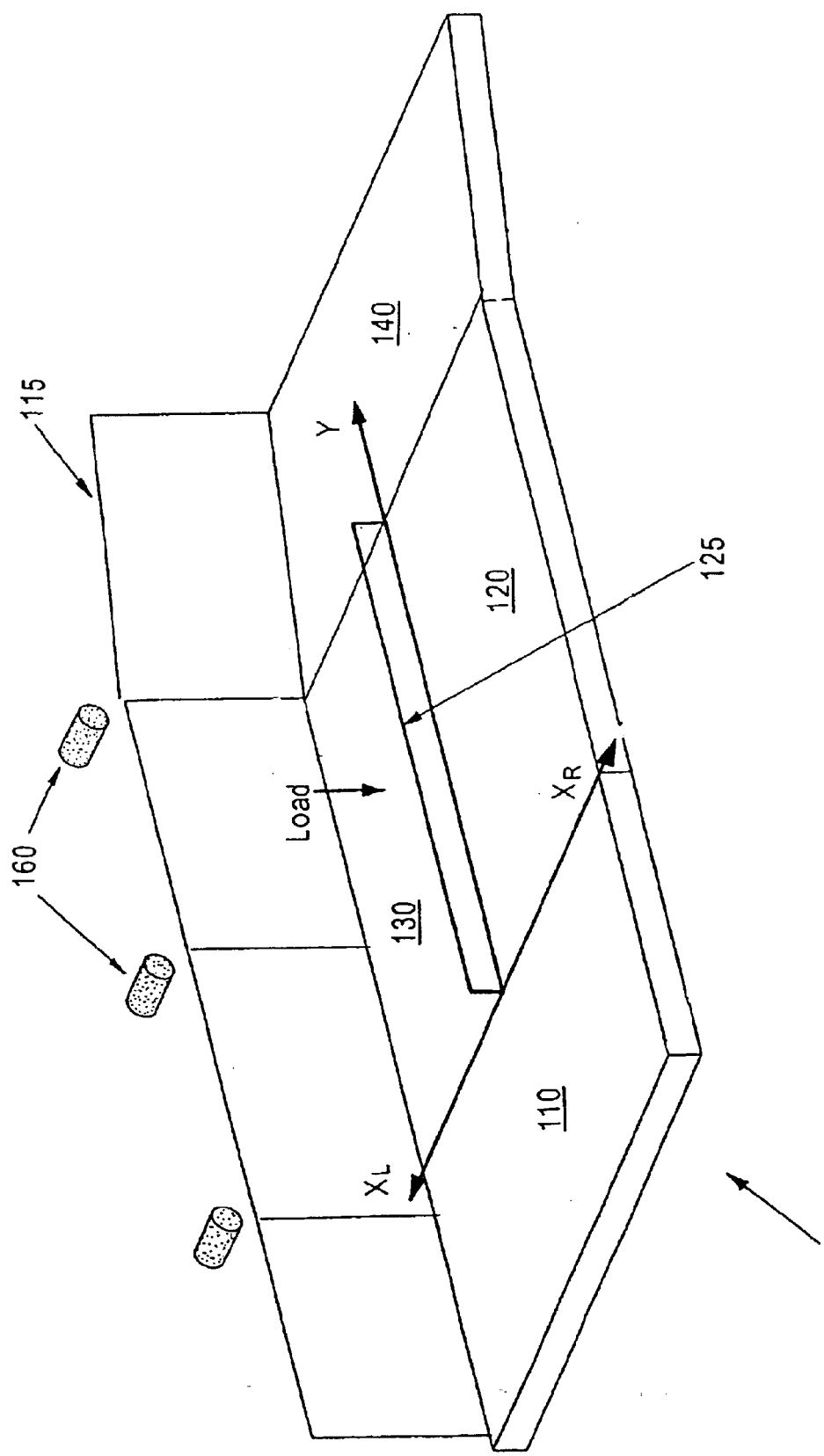
FIGS. 1(a)–1(c) are representations of a Reaction Force Detection (RFD) system that may be utilized in combination with the concepts disclosed herein comprising a isometric view, a side view, and a top view, respectively.
Figure 1B:
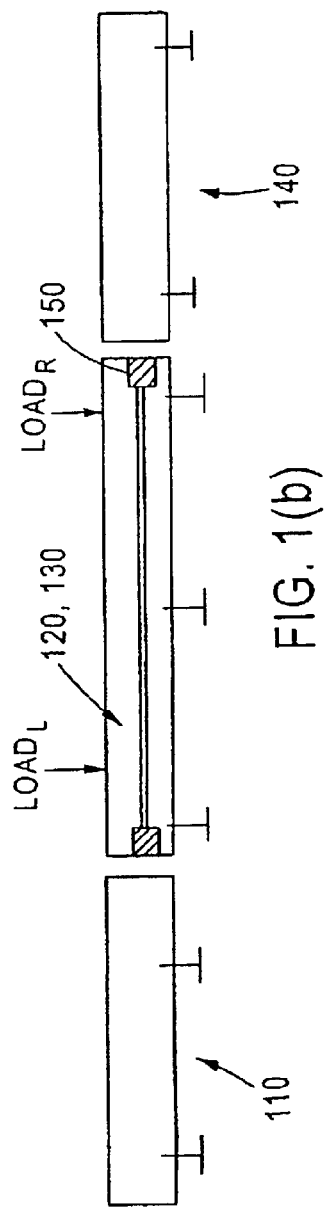
Figure 1C:
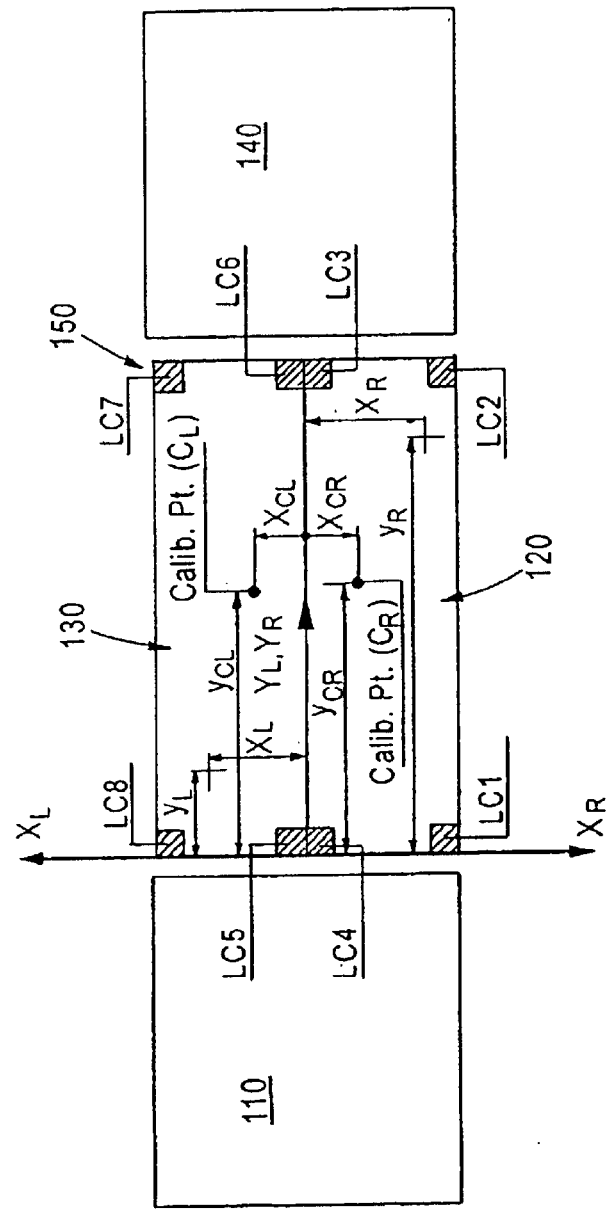

A Reaction Force Device (RFD) 100 advantageously adapted for use in accord with the present concept is depicted in FIGS. 1(a)–1(c). The RFD is configured to measure variables inclusive of the weight and forces related to walking gait of animals. As an animal passes through the RFD system, stepping on instrumented plates, the animal's limb reaction forces, weight, bilateral symmetry of limb reaction forces, and other factors may be determined, as discussed below and as discussed in the aforementioned "Method and Device for Analyzing Weight and Walking Gait", U.S. patent application Ser. No. 09/827,311, to Tasch et al., which is incorporated by reference herein in its entirety.

To facilitate the movement of a plurality of animals, impediments to animal movement (e.g., physical singulation) are advantageously omitted in the presently disclosed concepts. Side walls (e.g., 115) constrain an animal's lateral movement to thereby force the animal to walk over the plate and a divider 125 to prompts or forces, depending on height, the animal to place its left leg on a left plate 130 and right foot on a right plate 120 are still beneficial to a device used in combination with the concepts presently disclosed.

In one aspect, the RFD floor may comprise parallel left and right portions or plates 130, 120 optionally separated by a divider or partition 125 projecting upwardly from a position between the left and right plates, as shown in FIGS. 1(a)–1(c). The size and number of the plates may be varied so long as the configuration permits measurement of the ground reaction forces (GRFs) for all four of an animal's limbs in a single pass of the animal through the RFD.

As shown in the example of FIG. 1(c), each plate 130, 120 is supported by an array of four load cells 150 distributed adjacent the four corners of the respective plate 130, 120. The RFD may comprise more or less load cells 150 distributed in various locations and arrangements above, below, or adjacent the plates 130, 120. Load cells 150 measure the GRFs produced as the animal steps on each plate. The RFD system 100 measures these GRFs and calculates the position of the weight placed on the respective floor plate 130, 120.

As illustrated in FIG. 1(c), each of the plates 130, 120 comprises a separate coordinate system defined by ($X_L$, $Y_L$) and ($X_R$, $Y_R$), wherein ($X_{L,R}$, $Y_{L,R}$)=(0 cm, 0 cm) is arbitrarily located at the innermost corner of each of the plates 130, 120. In a preferred orientation of the working axes, X is positive in a direction toward the outside of the plates, Y is positive in a direction of the rear or backside of the plates, and Z is positive in an upward direction.

The position of a force applied to the plates 130, 120 is thus defined through the left and right coordinate systems ($X_L$, $Y_L$ and $X_R$, $Y_R$) shown FIGS. 1(a)–1(c). When a single limb (i.e., hoof or foot) is on a plate 130, 120, the RFD system 100 calculates the position of that limb. When more than one limb is in contact with a floor plate 130, 120, the RFD system 100 calculates the position of an equivalent or resultant force, as discussed below. For applications involving cows, Tasch et al. of the aforementioned "Method and Device for Analyzing Weight and Walking Gait", U.S. patent application Ser. No. 09/827,311, determined that the GRFs are substantially vertical and GRF variations due to lameness, or the onset thereof, are determinable based on differences in these vertical GRFs.

Load cell 150 outputs may be output to and analyzed by any conventional data acquisition devices, such as but not limited to an A/D board (e.g., an Iotech DaqBook model 200) receiving signals from an external eight channel strain gage module (e.g., an Iotech DBK43A). These eight channels are read, processed if necessary (e.g., amplified), and the sampled data stored in a conventional computer-readable memory device in a convenient form. The sampled and/or stored data may optionally be output through a communication interface or network link to an external system such as, but not limited to, a remote computer, remote storage device local network, host, ISP, or server. The sampling rate is freely variable, but should remain greater than the Nyquist rate, as known to those skilled in the art.

A velocity of the animal may be calculated using a transponder device, such as an incorporated into an ear tag or collar, attached to the animal (e.g., radio frequency identification devices (RFID)). As known to those skilled in the art, transponders function by replying to an interrogation request received from an interrogator, either by returning some data from the transponder such as an identity code or the value of a measurement, or returning the original properties of the signal received from the interrogator with virtually zero time delay, thereby allowing ranging measurements based on time of flight. For example, a base unit or interrogator may emit an energy pulse (e.g., a high intensity infrared pulse), as an interrogation request, at a designated frequency (e.g., 22 Hz), which triggers the transponder to emit a carrier wave bearing data (e.g., an ultrasound pulse) back to the base unit. The base unit may then measure the time difference between emission of the outgoing pulse (e.g., infrared pulse) and the arrival of the incoming pulse (e.g., ultrasound pulse), in a known manner. More elaborate systems inclusive of multiple bases (stationary sensors) to define a reference frame and global positioning systems could also be advantageously employed.

For convenience, the presently disclosed method and system for dynamic recordation and analysis of animal characteristics will described herein with particular emphasis on one aspect of such concepts, referred to using the shorthand "Softseparator", which represents a computer executable code or instruction set adapted to singulate animal data for further processing.

In one aspect, the Softseparator utilizes two input data files generated by the RFD system: an identification file (YYMMDDxxx.ID) and an analog file (YYMMDDxxx.ANA). The YYMMDDxxx.ID file stamps the time the data was recorded, the date and a running file number (xxx), the cow's transponder number, and the corresponding cow's number (see Table 1). By counting the repeated running file numbers (YYMMDDxxx), the number of cow records (n) in every file may be obtained. For the samples listed in FIG. 2 (Table 1), file 020527020 contains the records of two cows 199 and 1027 (n=2), file 020527021 contains the records of four cows 961, 217, 980, and 1026 (n=4), and file 020527022 of three cows 991, 213, and 885 (n=3). Once the number of records (n) of each analog file is determined, the Softseparator converts, via induction, the corresponding YYMMDDxxx.ANA file into n analog files. Each one of the converted files contains the LMVs of a single animal, as discussed in the following sections.

Figure 3:
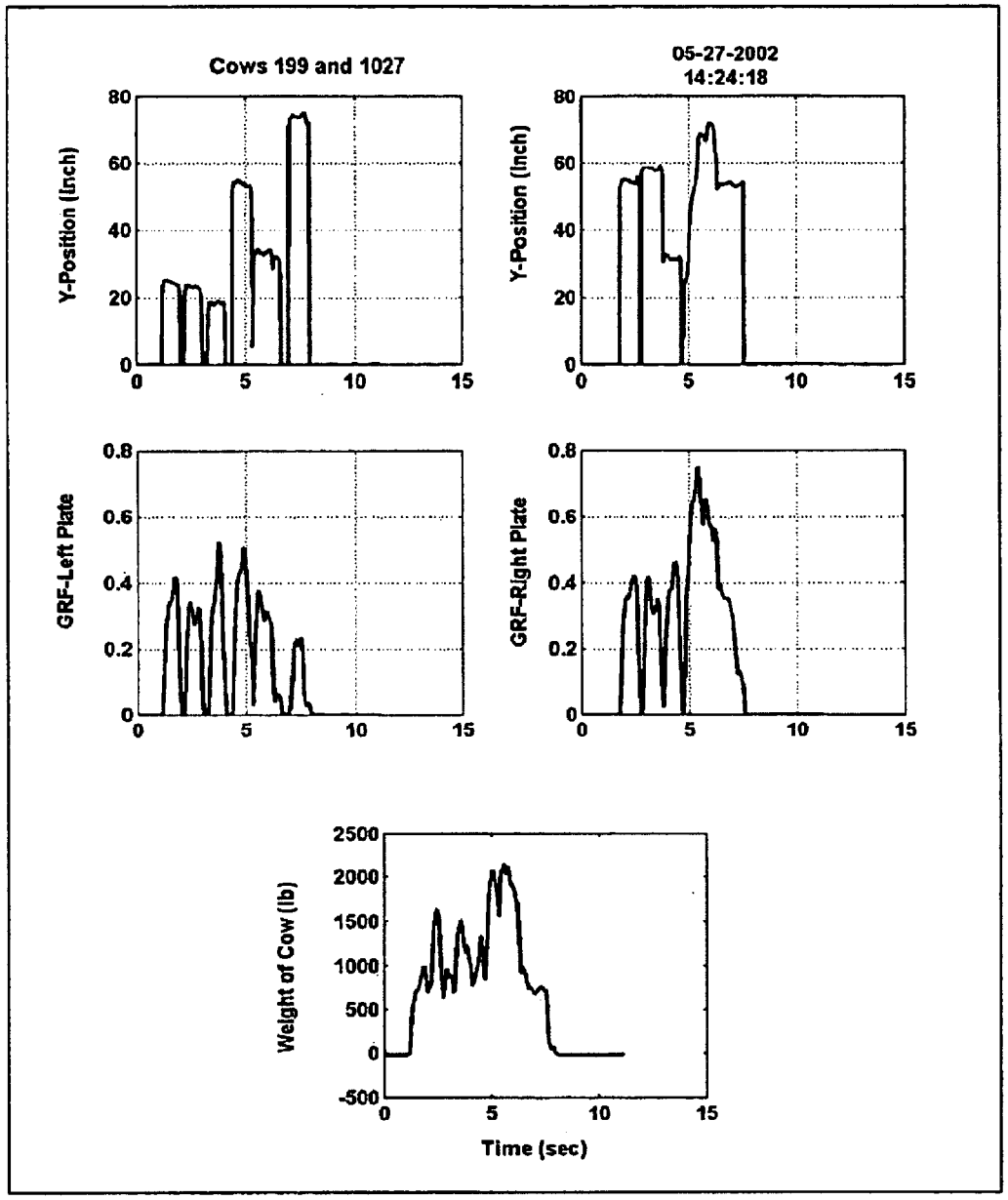
FIG. 3 shows Y-position, ground reaction force (GRF) and weight plots of cows 199 and 1027 recorded in one of the informational files shown in FIG. 2.
Figure 4:
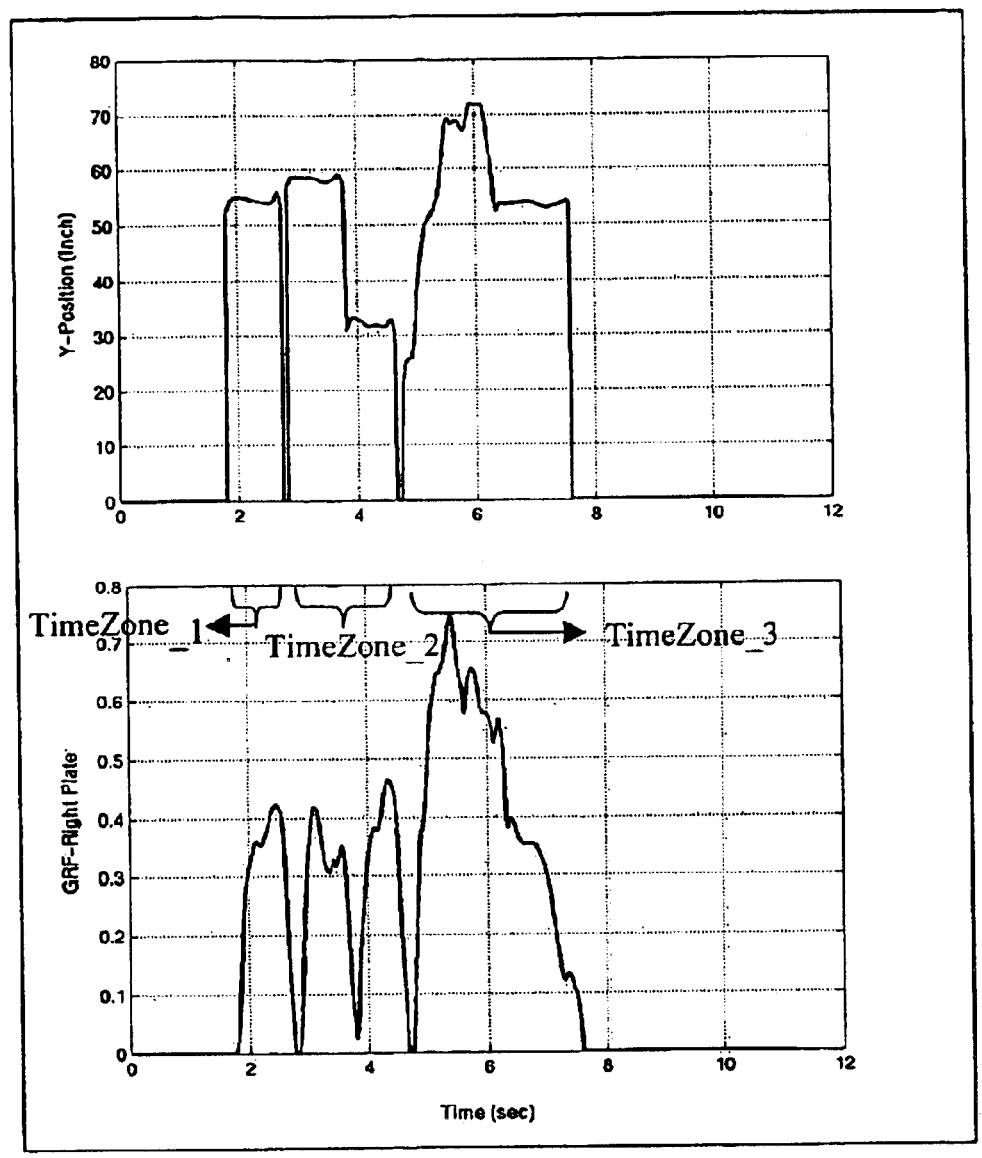
FIG. 4 shows the Y-position and GRF of the right plate for cows 199 and 1027, as well as the identification of $T_{START}$ and $T_{END}$ times for different TimeZones, in accord with the presently disclosed concepts.

Based on the LMVs recorded in YYMMDDxxx.ANA, Y position, ground reaction forces (GRF), and body weight plots are generated following the procedures discussed in Tasch et al., "Method and Device for Analyzing Weight and Walking Gait", U.S. patent application Ser. No. 09/827,311. FIG. 3 depicts the plots generated for the data recorded in file 020527$_{020}$.ANA. The start ($T_{Start}$) and end ($T_{End}$) times of each hoof/floor contact is determined by the TimeZones function. FIG. 4 depicts TimeZones 1, 2, and 3 that are recorded for the hoof/floor contacts of the right plate (see FIG. 3). The start and end times of these three TimeZones are, respectively, $T_{START}$=1.81 (TimeZone_1), 2.85 (TimeZone_2), and 4.76 (TimeZone_3) and $T_{END}$=2.74 (TimeZone_1), 4.65 (TimeZone_2), and 7.57 (TimeZone_3).

After identifying individual TimeZones, the LimbZoneStatistics function is called and thirteen statistical parameters, defined in FIG. 5 (Table 2) are evaluated for every LimbZone. As is obvious from the enumerated parameters, seven of the parameters assess Y position statistics and five GRF statistics. Based on these twelve (Y position and GRF) parameters the Softseparator determines the number of limbs (J_Limb) in each distinct LimbZone. The statistical parameters of the three LimbZones, shown in FIG. 4, are listed in FIG. 6 (Table 3). TimeZone_1 reflects a single limb, whereas TimeZone_2 and _3 reflect 2 and 3 limbs, respectively.

For adult dairy cows, the RFD in its current dimensions accommodates a length of less than two walking cows in a row. This limits the maximum limbs simultaneously contacting the left or right RFD floors to three. Hence, by accommodating 1, 2, and 3 limb contacts in any given LimbZone, one addresses all possible good, non-crossing over walks. Crossing over walks are presently discounted. However, the principles disclosed herein may be suitably scaled and/or modified in accord with the present disclosure to accommodate RFDs having dimensions permitting more than two walking cows, or other animals, in a row.

The number of limbs that contact the floor in any given LimbZone (J_Limb) dictates the selection of one of the following cases:

Case 1: When J_Limb=1, the SoftSeparator™ calls the LimbSequence function, and determines whether a given LimbZone is associated with a fore (F) or a hind (H) limb.

Case 2: If J_Limb=2, the SoftSeparator™ calls the TwoLimbSeparation function and the LimbZone is divided into two separated single limb zones. The LimbSequence function is then used to associate the separated limb zones with either a fore (F) or a hind (H) limb.

Case 3: In case J_Limb=3, the ThreeLimbSeparation function is activated, and the LimbZone is separated into three single limb zones. This is followed by a LimbSequence call that designates the fore and hind limbs with F and H, respectively.

In FIG. 6 (Table 3), TimeZone_1 is identified to be a single limb zone, and the LimbSequence function designates it as a fore (F) limb. The second TimeZone is a two limb zone (J_Limb=2), and therefore TwoLimbSeparation function converts it into two single limb zones (see FIG. 7(c)). FIGS. 7(a)–7(c) show Y position and GRF plots of TimeZone_2 (see FIG. 4) before separation are represented by reference numerals (a) and (b), respectively. The TwoLimbSeparation function separates the two limb zone into two single limb zones. The GRF plots for the separate zones are shown in FIG. 7(c). The LimbZoneStatistics of the two separated time zones (TimeZone_21 and TimeZone_22) are evaluated, and the LimbSequence function determines the limbs that contact the floor at TimeZone_21 and TimeZone_22 to be hind (H) and fore (F), respectively (see FIG. 8 (Table 4)).

After identifying the limb sequence to be F, H, and F (see FIG. 8 (Table 4)) NewCowCheck is activated and it determines whether the limb sequence belongs to one or two cows. The assumption is that the animals do not walk backward; hence, when a hind (H) limb is followed by a fore (F) limb, the latter is assumed to belong to a new different animal.

Therefore, TimeZone_1 and _21 belong to the first animal (Cow 199, in this case), and LimbZones_22 and _3 belong to the other (n−1) cows. In this case n=2 and, therefore, the latter two limbs belong to the second walking cow (Cow 1027, see FIG. 8 (Table 4)).

This iterative algorithm is applied to both left and right floors, and as a result, the LMV records depicted in FIG. 3 can be separated into two individual files, the Y position, GRF, and body weight of which are shown in FIGS. 9(a)–(b). Note that FIGS. 9(a)–(b) show, respectively, Y position, GRF, and body weight plots of the two separated LMVs records of cows 199 and 1027. Note that the body weight plots reflect two, four, and two limb weights that reflect a successful separation. A successful cow separation will result in body weight plots that reflect a weighing sequence of two (fore) limbs, four (fore and hind) limbs, and two (hind) limbs, as shown in FIGS. 9(a)–(b).

Figure 10A:
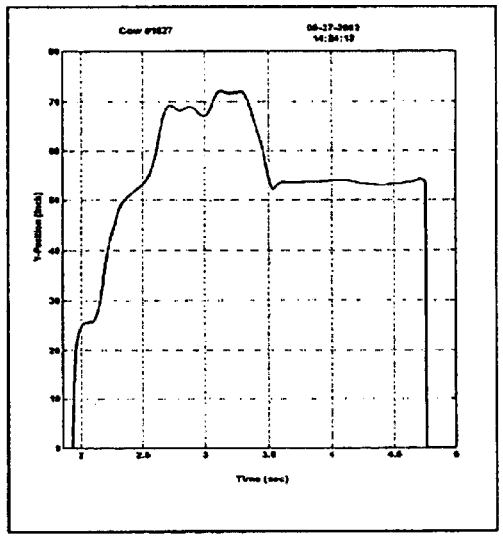
FIGS. 10(a)–(b) depict Y-position and GRF plots of TimeZone_3, shown in FIG. 4, before separation by the ThreeLimbSeparation function.
Figure 10B:
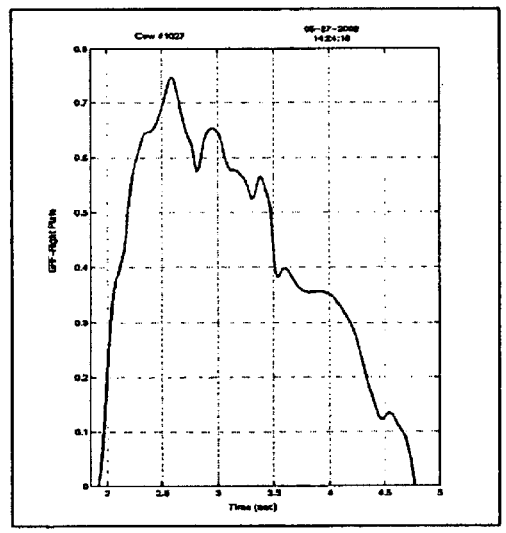
Figure 10C:
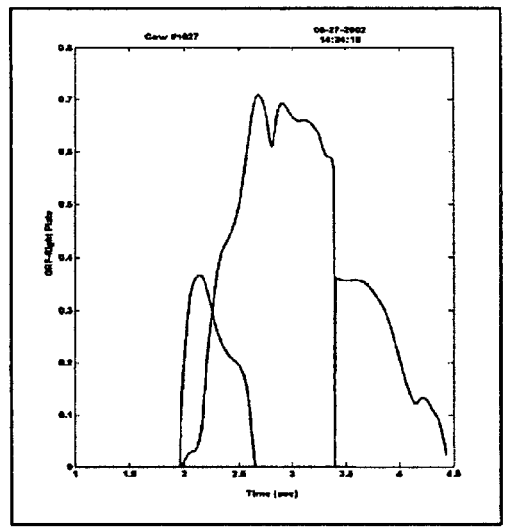
FIG. 10(c) depicts GRF plots for the three single limb zones following separation by the ThreeLimbSeparation function, in accord with the present concepts.
Figure 11A:
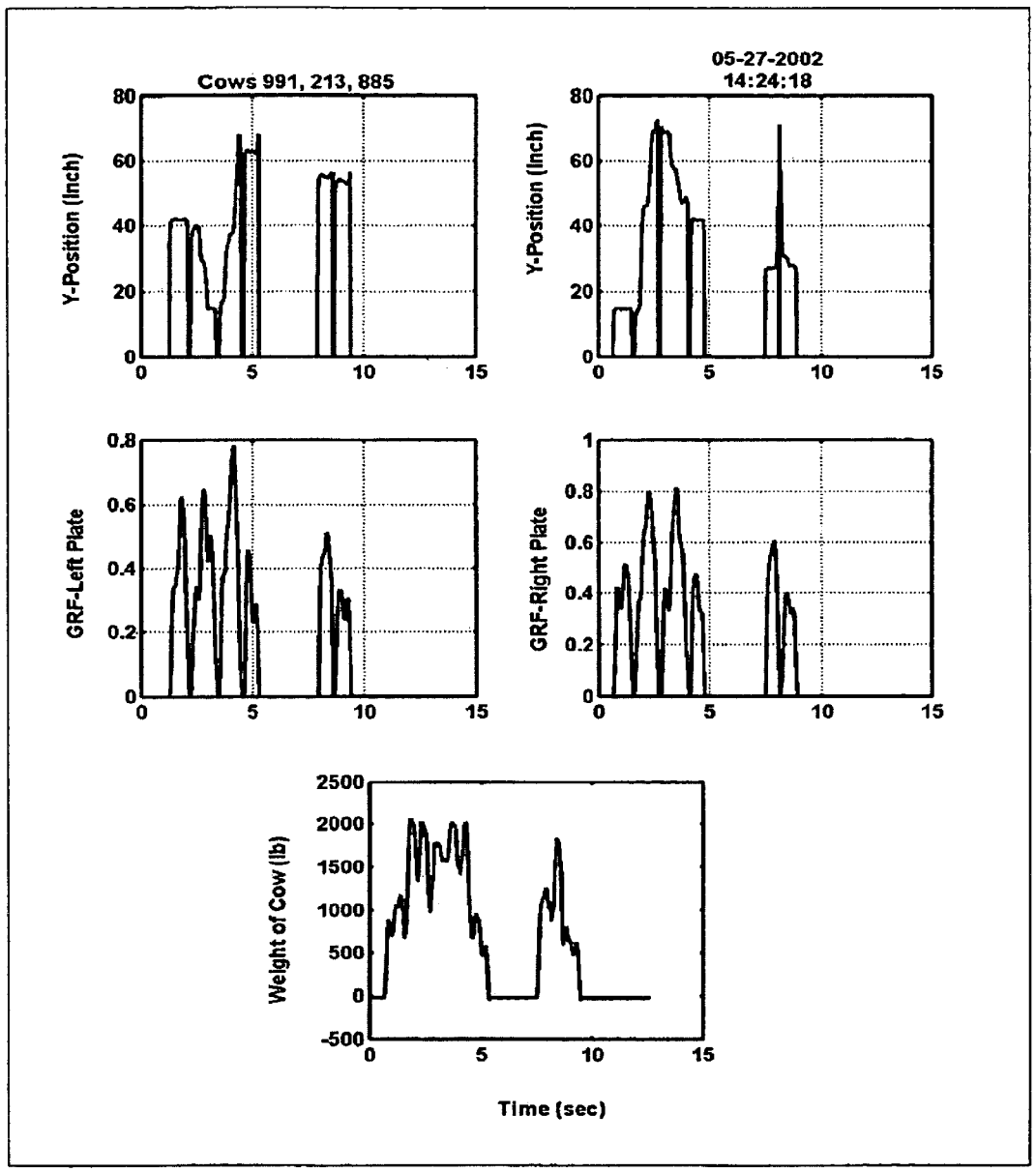
Figure 11B:
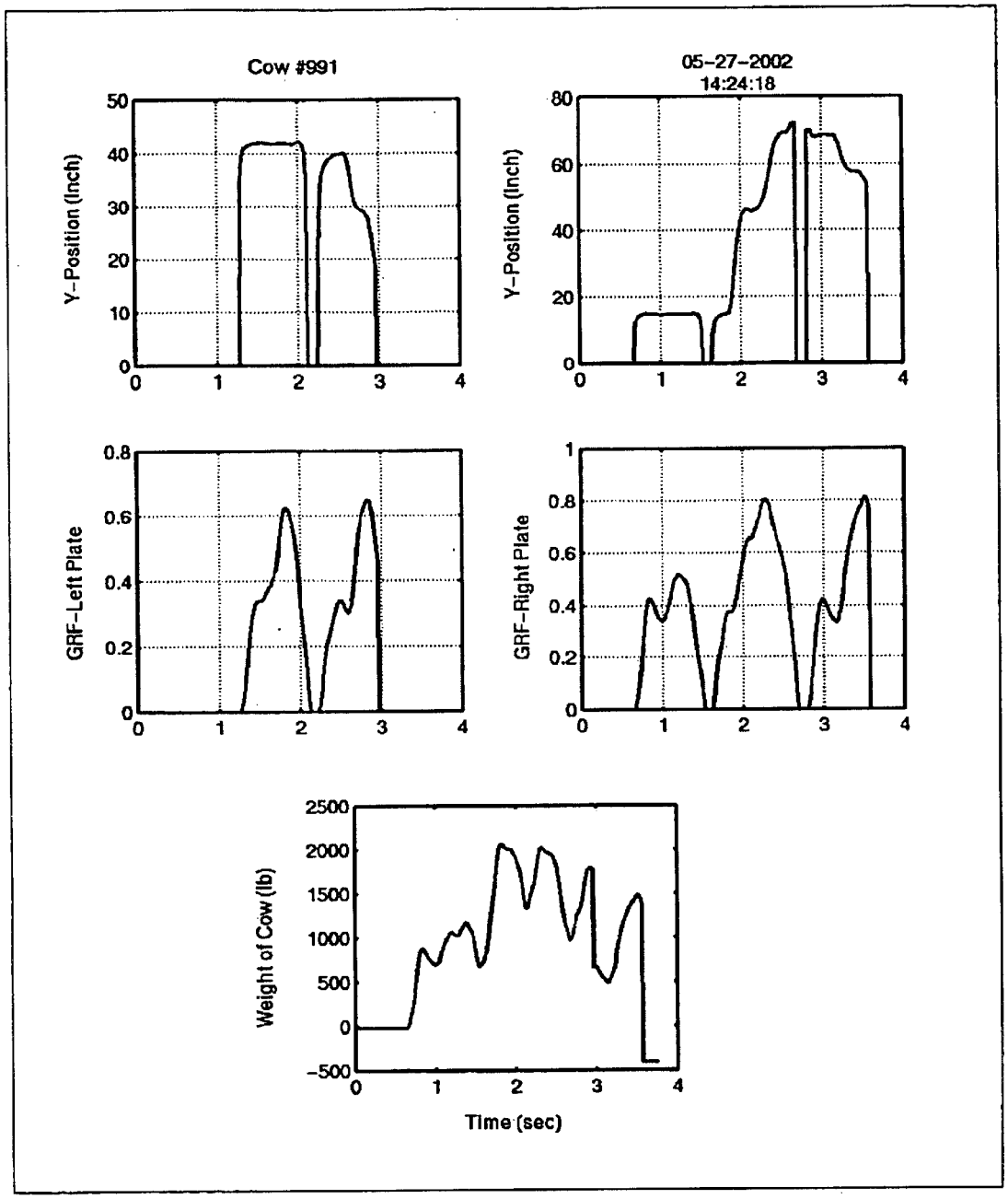
Figure 11C:
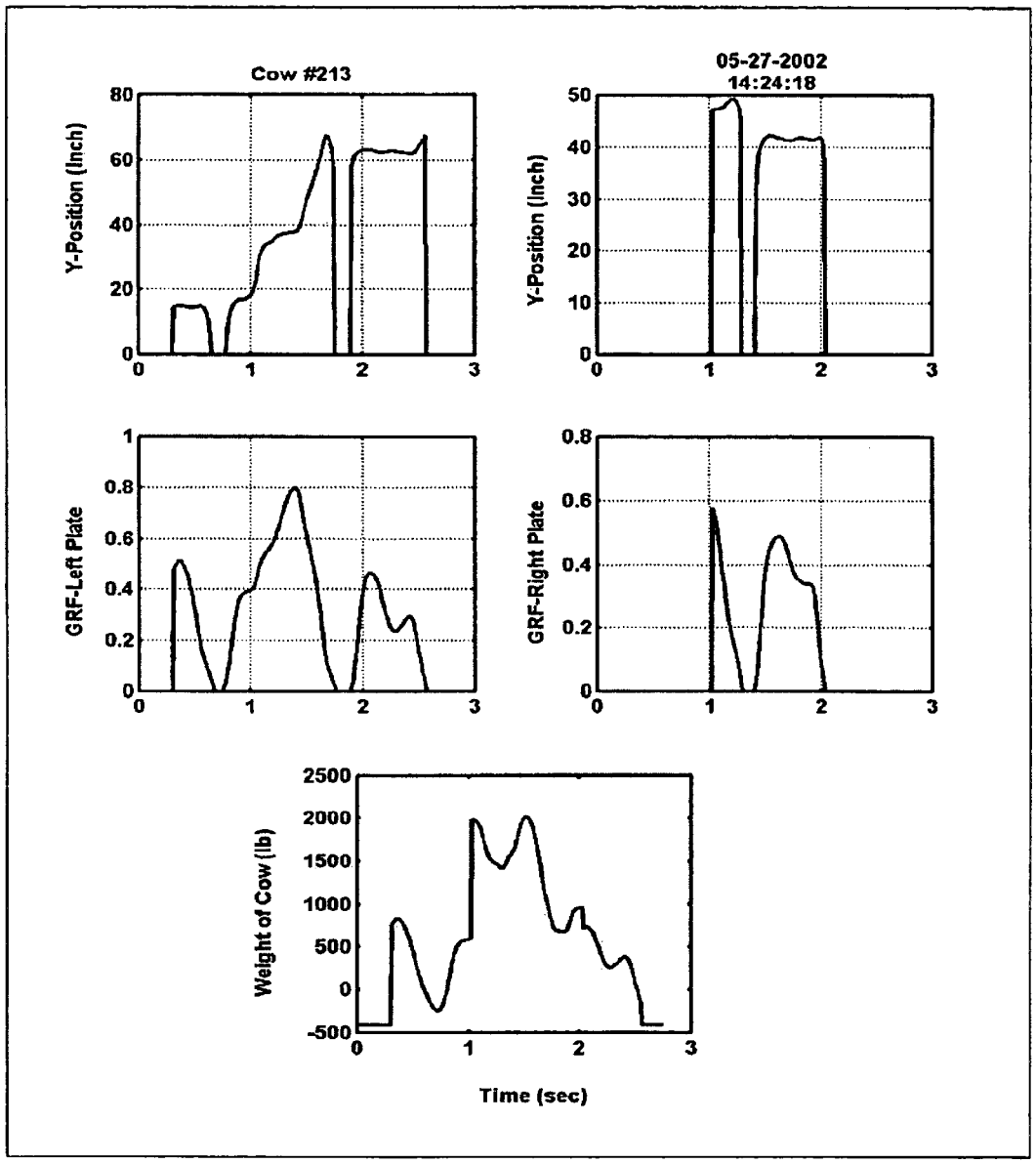
Figure 11D:
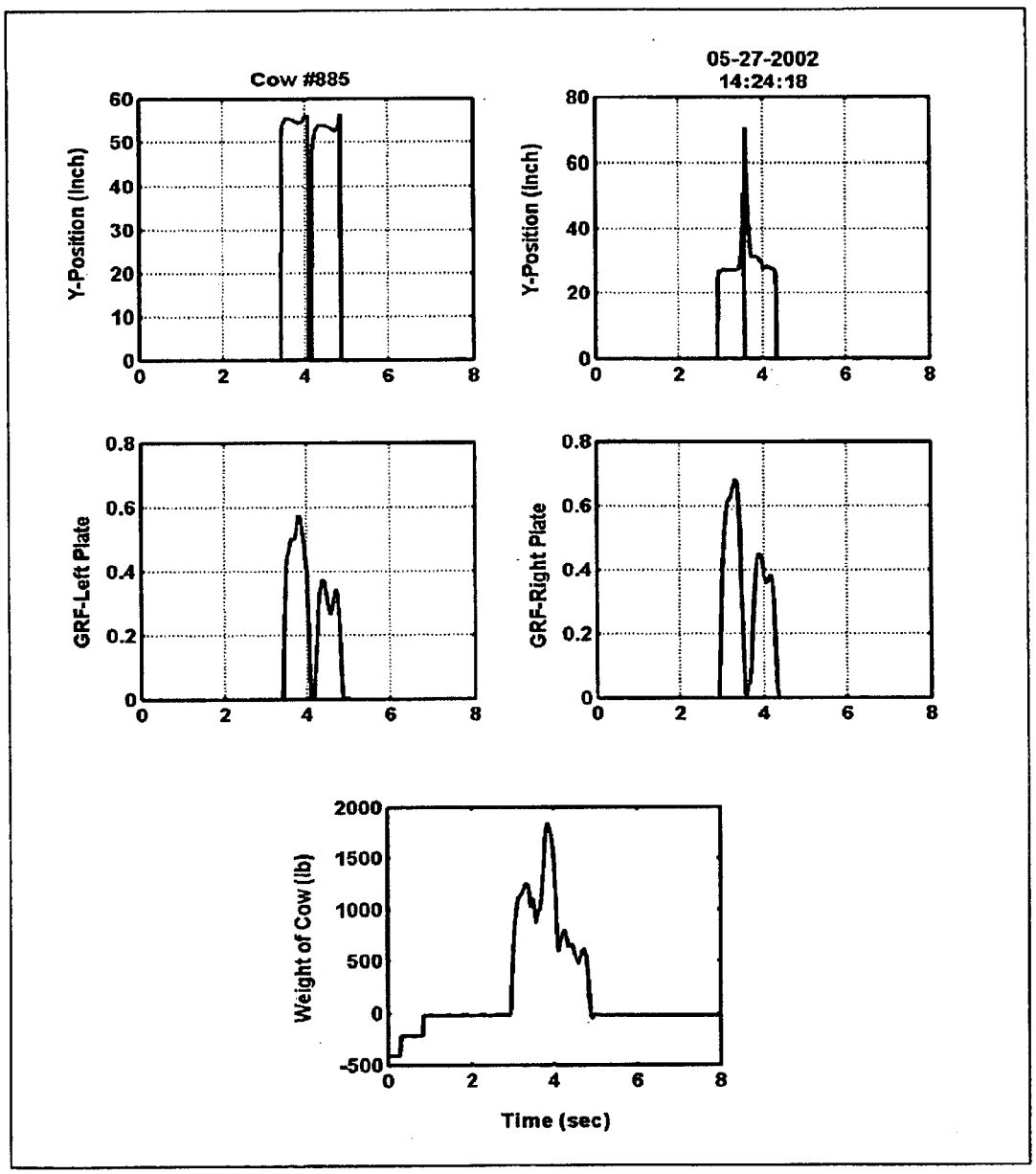
Figure 12A:
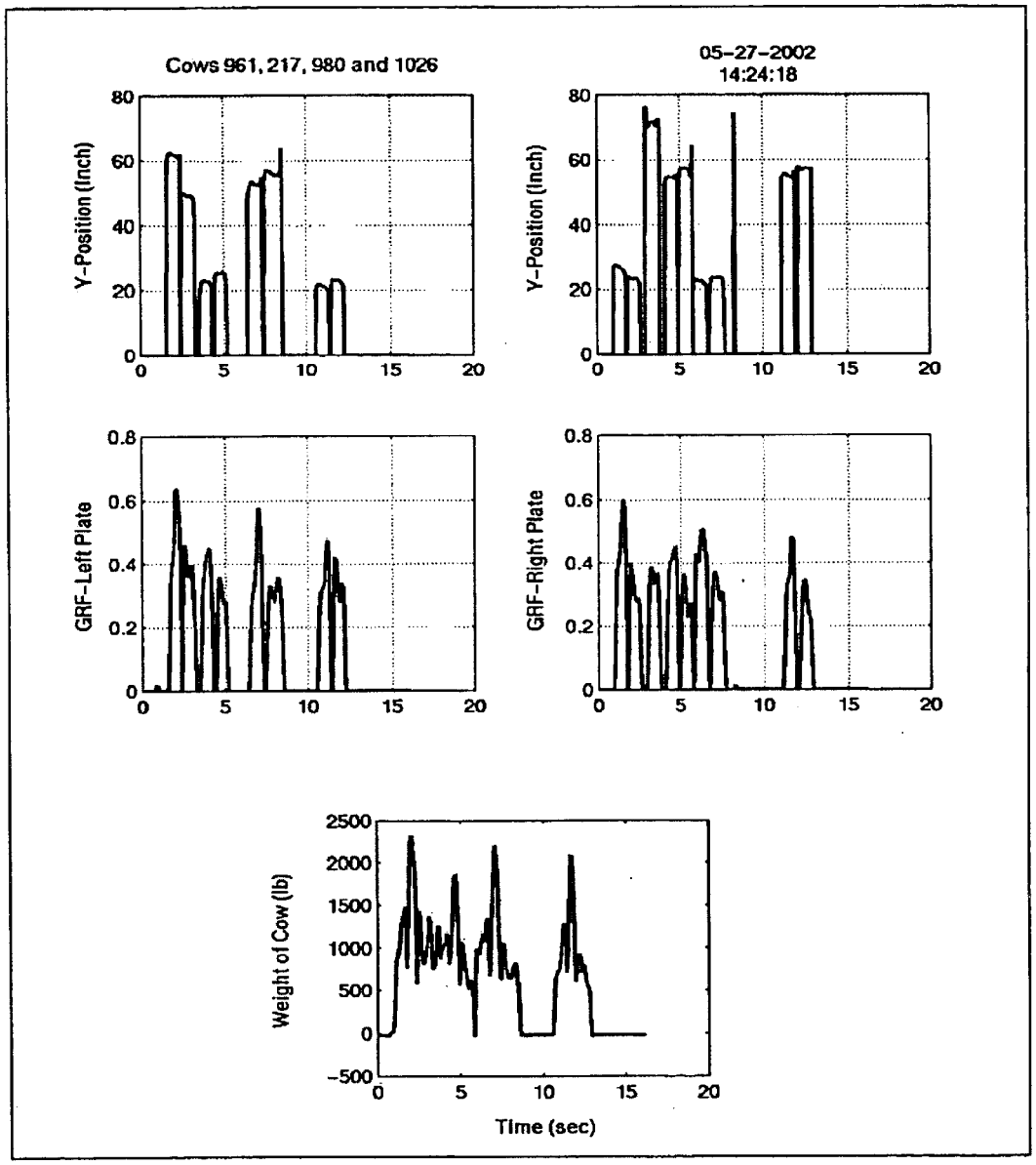
FIG. 12(a) is the records of four cows and FIGS. 12(b)–(e) respectively show Y-position, GRF, and weight plots of individual cows 961, 217, 980 and 1026.
Figure 12B:
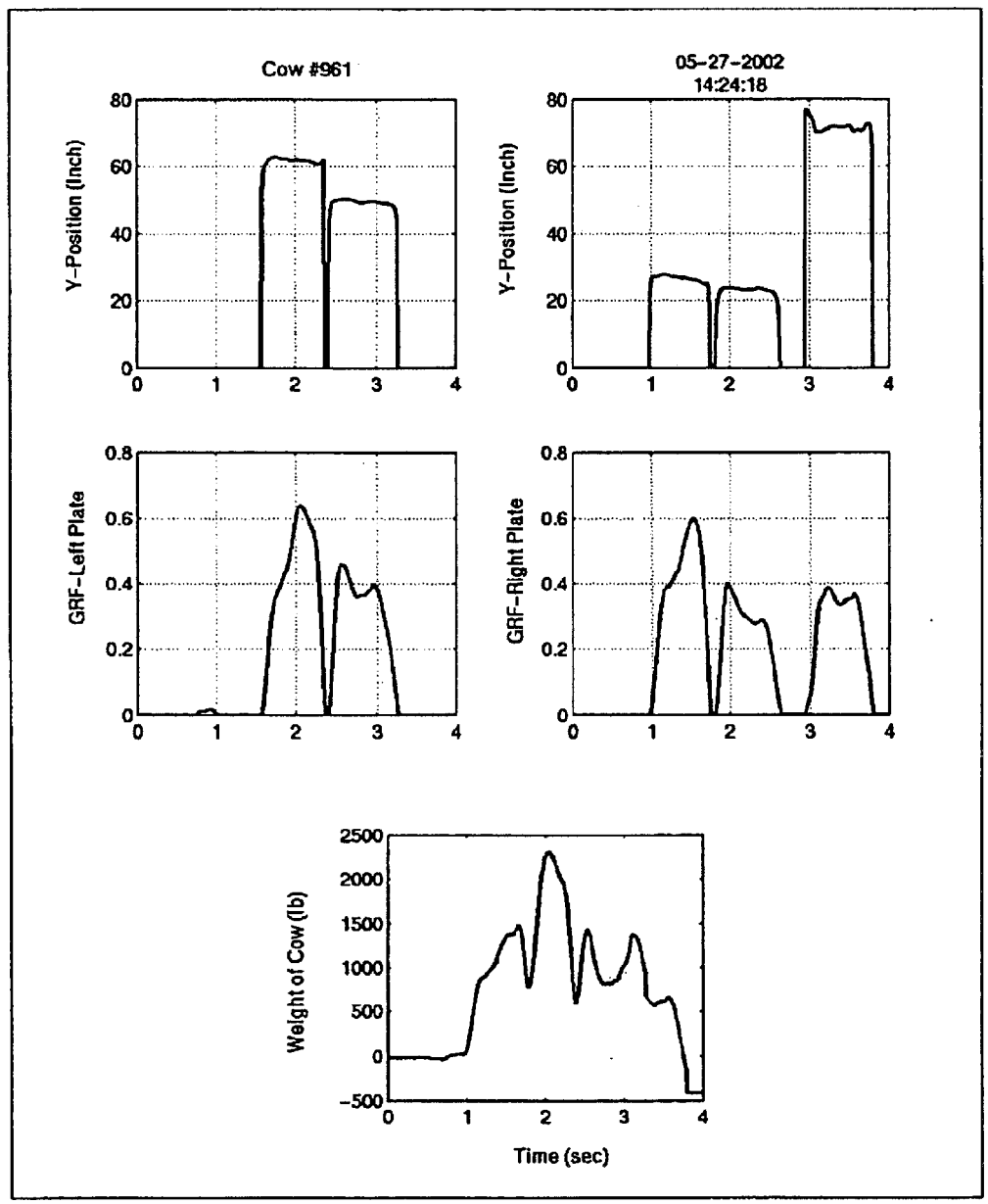
Figure 12C:
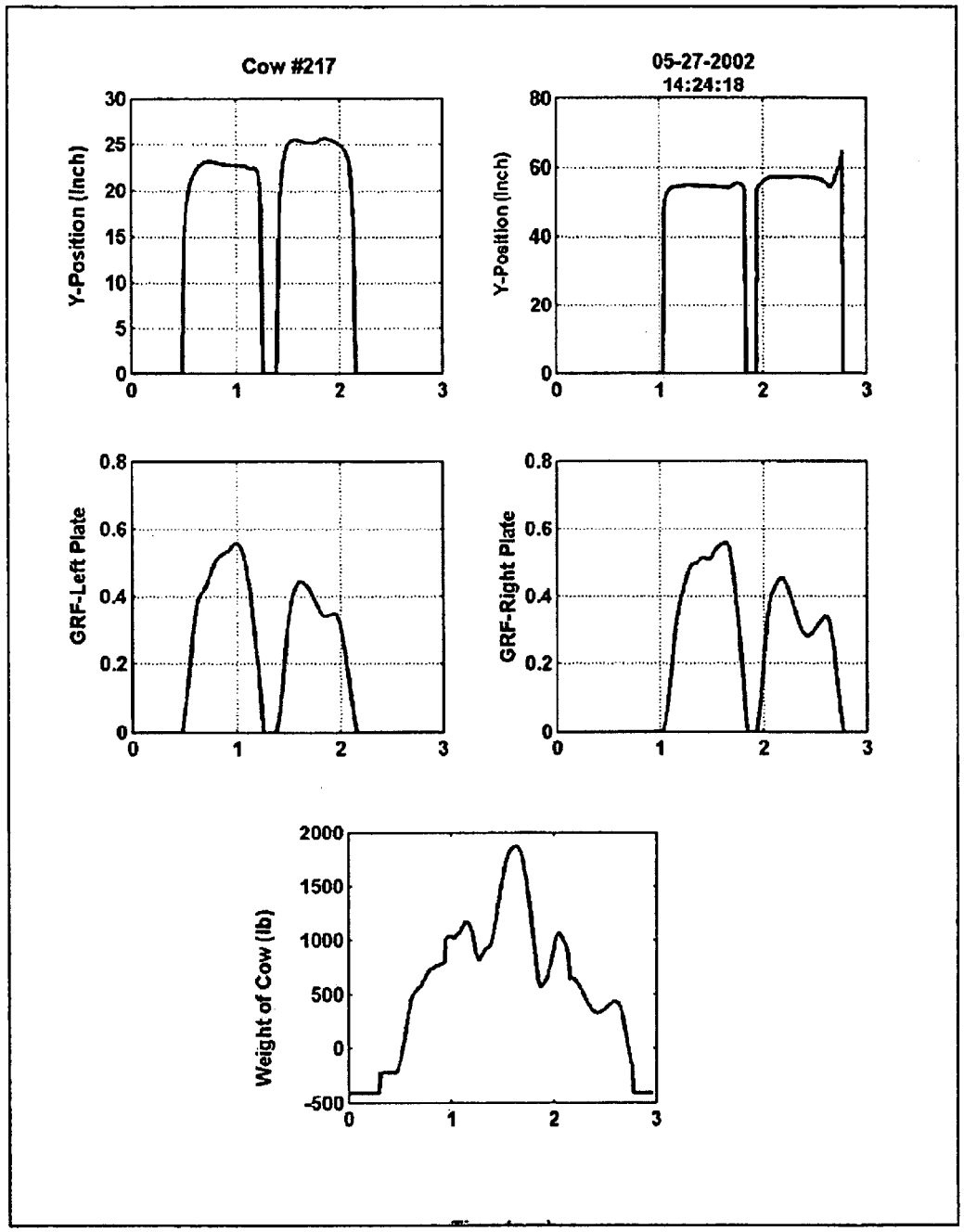
Figure 12D:
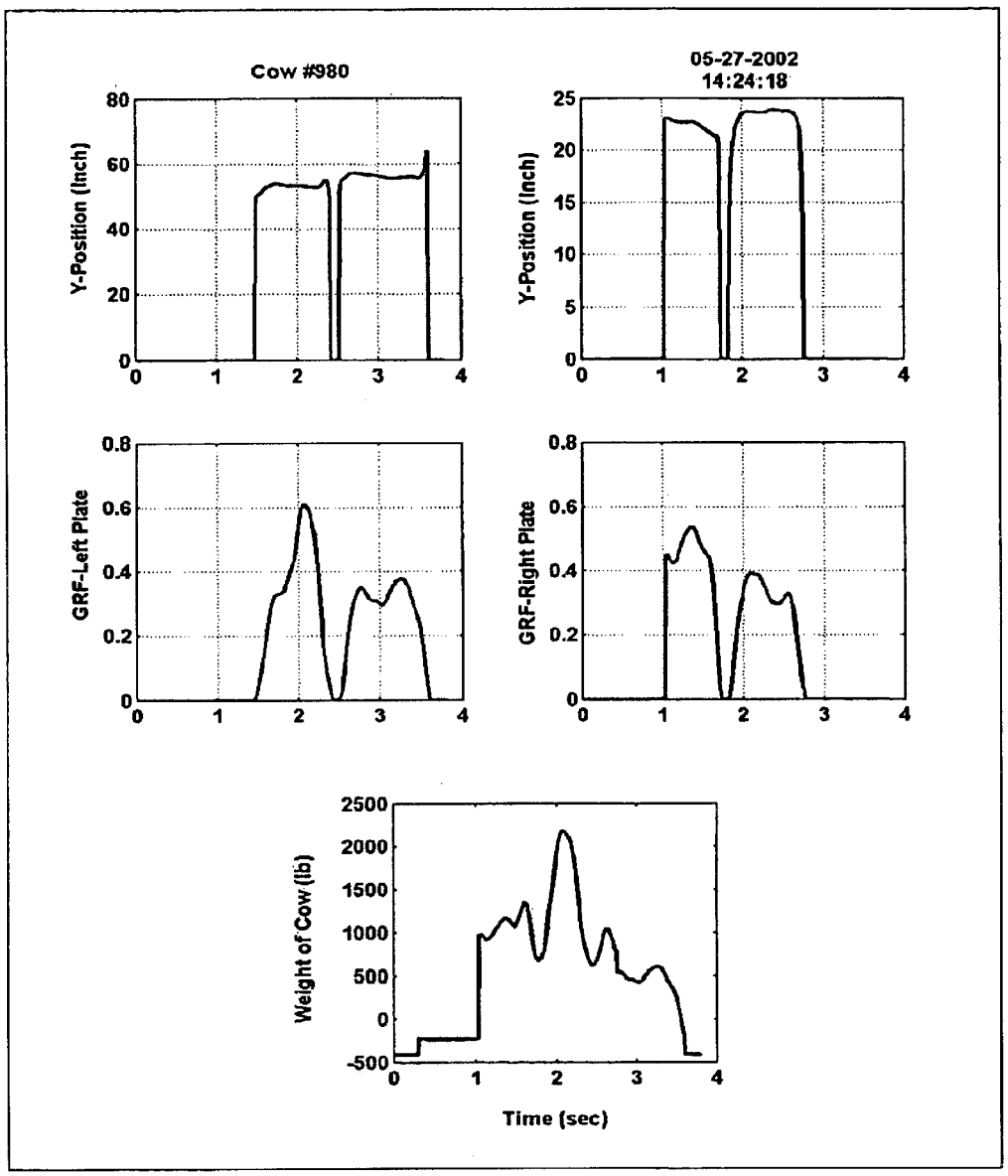
Figure 12E:
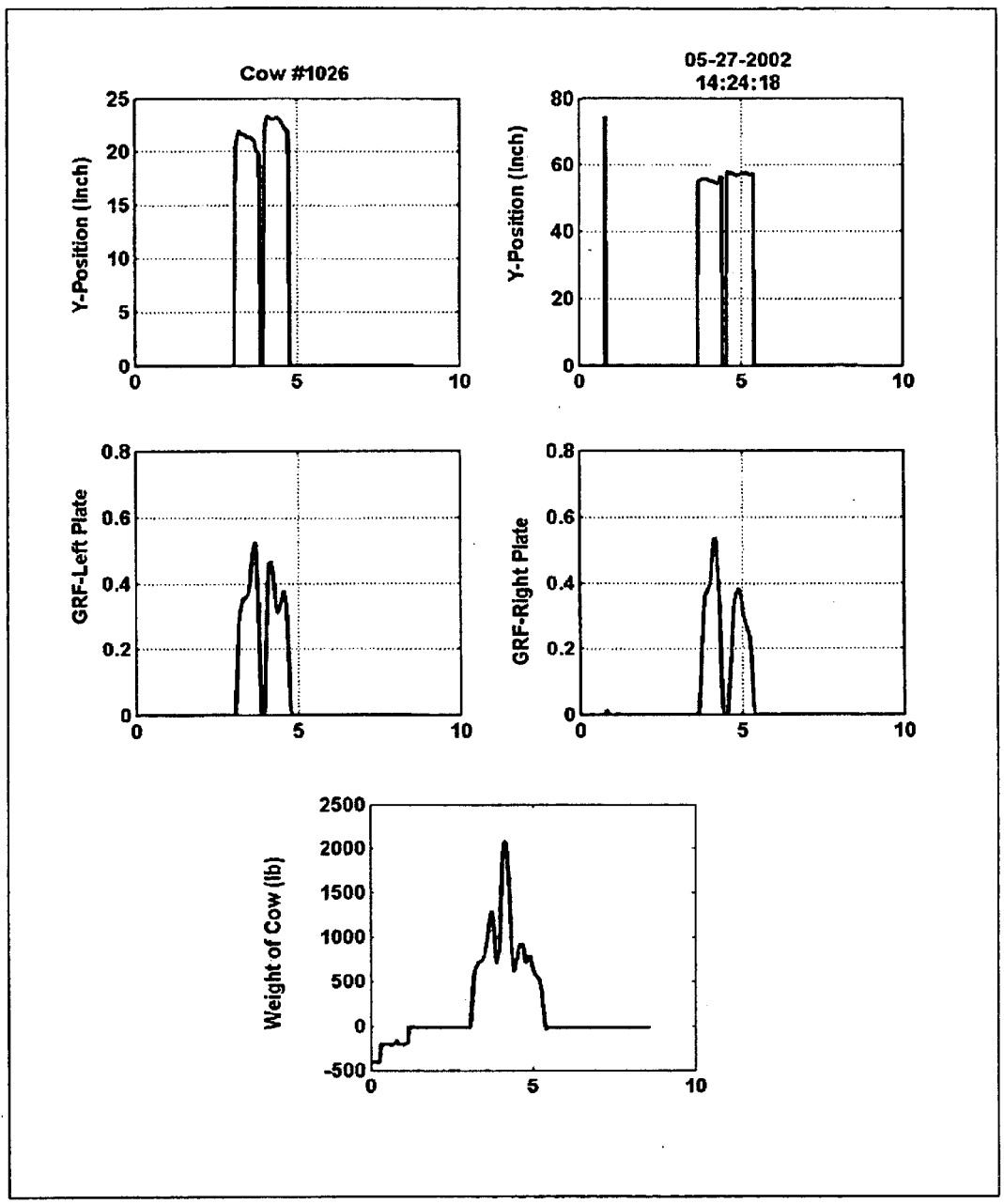

In case J_Limb of a given LimbZone is 3, the ThreeLimbSeparation function is activated, and the LMV records are separated into three single limb zones, as depicted in FIG. 10(c). Similar to the TwoLimbSeparation procedure, the SoftSeperator in this case calculates the limb zone statistics, determines the limb sequence, and identifies records of new cows.

Further, to the above, the SoftSeparator was applied to two groups of three and four cows. The record of the three cow group and its separation into individual files are shown in FIGS. 11(a)–(d). The record of the four cow group is shown in FIGS. 12(a)–(e). Separation the body weight plots in these three and four cow groups reflects the weight of two, four, and two limbs, an indication of successful animal separation.

The SoftSeparator therefore separates the LMV record of animals that walk through a reaction force detection system in groups into multiple records of individual animals. Such algorithm or executable coding eliminates the need for gates or other physical impediments that slow down animal traffic. The aforementioned exemplary case studies demonstrate that the SoftSeparator operates for groups of two, three, and four cows, and that the concepts therein are extendable, by induction, to address animal groups of any size.

In one aspect, the system plots Y position, GRF, and body weight versus time. The latter plot can be used as a measure of success in separating the animal records. Body weight plots of a single, separated animal reflects the weight sequence of two, four, and two limbs. Any deviation from this pattern is associated with LMV records of more than one animal or, in other words, unsuccessful animal separation.

In the following disclosure, extensive reference is made to particular elements of an exemplary coding and commands premised upon MATLAB®, a conventional environment for engineering and science applications enabling efficient data acquisition and analysis, integration of mathematical computing and visualization, and permitting fast access and importation of data from instruments, files, and external databases and programs (e.g., external routines written in C, C++, Fortran, and Java). Although MATLAB® is used in the example set forth below, other conventional coding languages could also be advantageously used in accord with the disclosed concepts.

Figure 13:
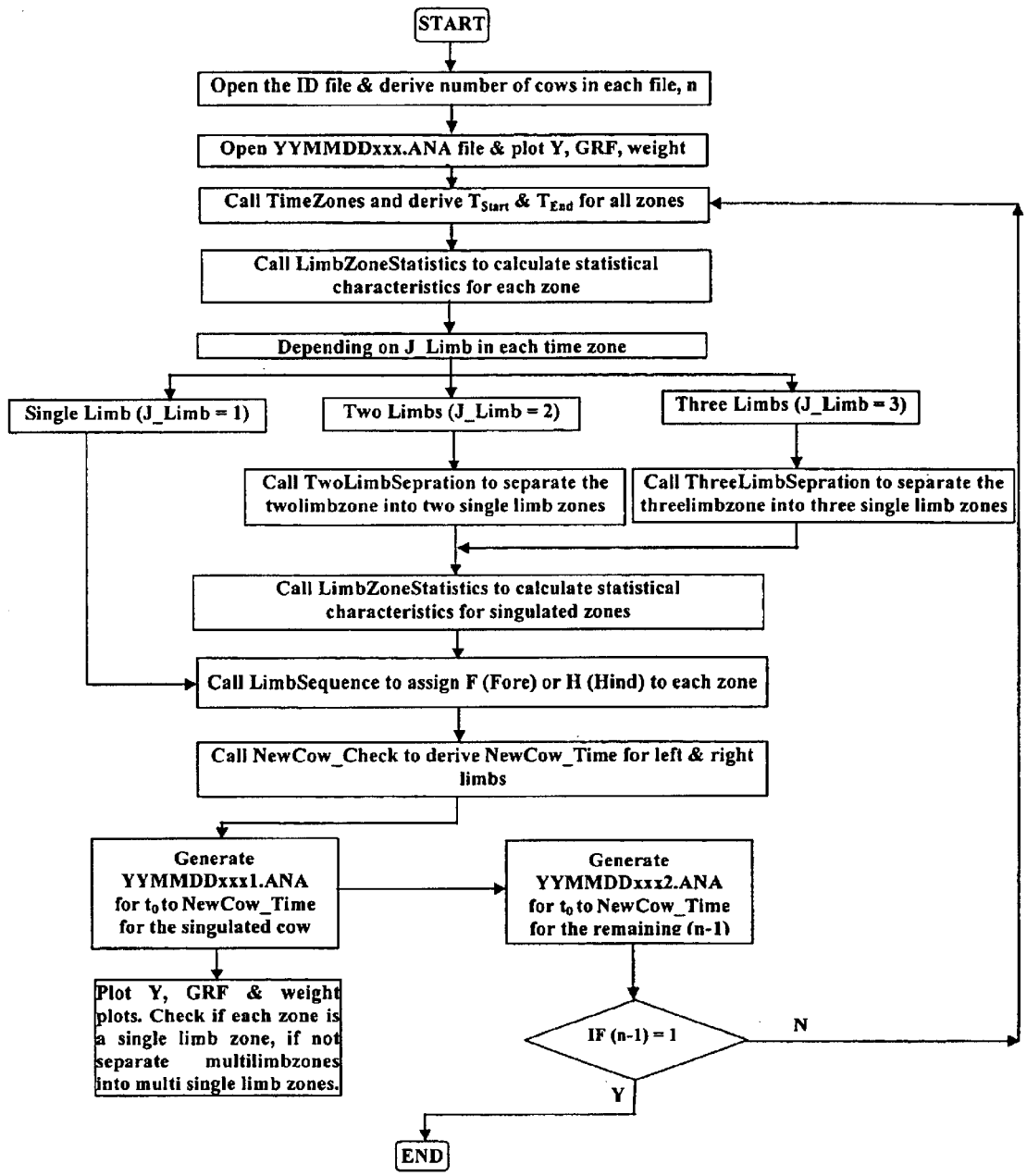
FIG. 13 shows a flowchart for an example of logical operations in accord with the presently disclosed concepts.

FIG. 13 is a non-limiting example of logical operations (i.e., a flowchart) in accord with the Softseparator embodiment of the concepts disclosed herein. All file names and variable names are arbitrary and may be freely varied in a manner known to those skilled in the art. Further, the order of execution of various subroutines, callouts, and sequences may be varied in accord with the present concepts in a manner consistent with the knowledge of those of ordinary skill in the art.

A short summary of the various SoftSeperator subroutines is now provided to facilitate the subsequent disclosure. The Softseparator main program or subroutine opens the raw data file and calls other functions. The xygrfplot.m function calculates X, Y positions of placement of limbs and associated ground reaction forces and plots them as a function of time. The TimeZones_LEFTRRIGHT.m function calculates the start and end times of every timezone. The LimbZoneStatistics.m function calculates various limbzone statistics for each timezone. The TwoLimbSeparation.m function, in instances where there are two limbs in a given time zone, separates the two-limb-zone into two zones each with a single limb. The LimbZoneStatisticsfortwolimb.m function calculates various limb zone statistics for two single limb time zones after the separation of the two limb zones. The ThreeLimbSeparation.m function, in instances where there are three limbs in a single time zone, function separates the three-limb-zone into three zones of a single limb. The LimbSequence_LEFTRIGHT_Check.m function assigns a single limb zone as a fore or hind limb. The NewCow_LEFTRIGHT_Check.m function checks if the data belongs to the same or a different new cow. The Cows_separation.m function separates the raw data for a new cow from the database.

I. Main Program

In main program, shown in FIG. 13, an _.ID file is opened and the number, n, of cows present in each of the files is derived. A subroutine reads data from the _.ID file using, for example, a MATLAB® textread command and stores it in a character format using char command. The number of total cows in the _.ID file is stored in a variable named D_index. A loop starting at 1 and going up to D_index is initiated and the number of cows recorded in each file is determined. This is obtained by determining the number of times a given file number appears in the _.ID records. The file number is, in one aspect, the $3^{rd}$ character in the line of the _.ID file. The number of cows in each loadcell file is written into a matrix "dc".

A loop of p=1 to length(dc) is then started. In this loop the load cell record (filename.ANA) and photocell data (filename.DIG) are opened. An animal identification number is read along with date_str and time_str, which are recorded into a variable named datetime. The calibration factors are also read (zero, slope, and updated_zero) and recorded into a twenty four entry matrix named cal_factors, as well as a file named calibr.DAT. The total number of characters written into the variable char_raw_data is calculated using the length command, and the length of this file is recorded in the variable last_index. A file loadcell.dat is opened and a loop is started where i=29 to (last_index−3). In this loop, the character format of the raw loadcell data is converted into a number format written into eight columns. This eight column data file is named loadcell.dat and it is closed. The files Calibr.dat and loadcell.dat are loaded into the RAM of a processor or processors executing the code and the loadcell raw data values are converted into an appropriate weight measure (e.g., lb units) using the relation:

$$LCi = \text{loadcell} * \text{slope} + \text{zero} \quad (1)$$

LCi is a matrix that records the time record (in sec) in the $1^{st}$ column, and the loadcell values (lb) in matrix columns 2–9.

The main program calls a function cows_separation. If input to this function is the data of multiple cows then, this function returns the loadcell raw values of remaining cows by separating the first cow to a separate cowseparation variable until the latter contains data of a single animal. The loop of the main program terminates when cowseparation contains data of a single animal.

II. TimeZones_LEFTRIGHT

The following variables are passed to the function TimeZones_LEFTRIGHT; Y position (LEFTRIGHT_Y) and the corresponding GRF values (LEFTRIGHT_GRF).

A MATLAB find function returns a vector of indices for which Y position of either right or left limb greater than zero (LR_Y). The minimum and maximum values of LR_Y vector are identified and stored into LR_tS and LR_tE, respectively.

The difference between the vector of indices for which Y position is greater than zero is calculated and stored into diff_LR_Y (e.g., for LR_Y=find(LEFTRIGHT_Y>0), LR_tS=min(LR_Y) and LR_tE=max(LR_Y). A find function is again used to identify the indices for which the difference vector is greater than one and is stored in a variable named diff_LRY (e.g., (diff_LRY=find(diff_LR_Y>1)). The subroutine then executes loops comprising a first case (case 1) wherein only one limb is on the right side or left side, a second case (case 2) wherein more than two limbs are on the right or left side, and a third case (case 3) wherein two limbs are on the right side or left side.

For case 1, if the length of the vector diff_LR_Y is zero (e.g., If (length(diff_LRY)==0)), then the examined Y position is continuous. The LR_tS is stored into LRt(1) and the LR_tE is stored into LRt(2). LRt(x) is a vector variable representing the limbs in a limb zone. LRt(1) and LRt(2) reflect, in this case, only one limb on either the left or right side.

For case 2, an "elseif" loop is executed. Elseif the length of diff_LRY is greater than one, a loop is initiated for which i=0 up to (length(diff_LRY)−2). LRt(1) is equated to LR_tS and LRt(2) is equal to the minimum of LR_Y plus diff_LRY((1)−1). LRY(1) is the first number in the LRY vector. LRt(2*i+3) is equated to LRt(2*i+2) plus (diff_LR_Y(diff_LRY(i+1). Also, LRt(2*i+4) is equated to LRt(2*i+3) plus (diff_LRY(i+2)−diff_LRY(i+1))−1), at which point the loop ends and the loop index i is incremented by one (i=i+1). LRt(2*i+3) is then equated to LRt(2*i+2) plus diff_LR_Y(diff_LRY(i+1)) and LRt(2*i+4) is set equal to LR_tE.

For case 3, an else loop is executed. Else LRt(1) is equated to min(LR_Y), LRt(2) is equated to (min(LR_Y)+diff_LRY(1)−1), LRt(3) is equated to (LRt(2)+diff_LR_Y(diff_LRY(1))), and LRt(4) is equated to LR_tE.

As one example of the above subroutine, if there are two limb zones and there are more than two limbs represented therein, the computations will stay within a loop having consistent treatment. In this example, the first limb zone will start from index 5 and end at 10 and the second limb zone will start from index 15 and end at 20. The LR_Y vector (if Y>0) will be defined as 5 6 7 8 9 10 15 16 17 18 19 20 25 26 27 28 29 30. From this sample vector, LR_tS=5 (min (LR_Y)) and LR_tE=30 (max(LR_Y)). Diff_LR_Y, the difference of indices where Y>0) yields 1 1 1 1 1 5 1 1 1 1 1 5. Diff_LRY (indices for which diff_LR_Y>1) then yields 6 12. For the assignment of times for different time zones, LRt(1)=LR_TS and LRt(2)=LR_tS+diff_LRY((1)−1), which is (5+6−1) or 10. As noted above, LRt(2*i+3)= LRt(2*i+2)+(diff_LR_Y(diff_LRY(i+1))). Also, LRt(2*i+4)=LRt(2*i+3)+(diff_LRY(i+2)−(diff_LRY(i+1))−1). If i=0, LRt(3) is then equal to LRt(2)+(diff_LR_Y(diff_LRY(1)))=10+(diff_LR_Y(6))=10+5=15. LRt(4)=LRt(3)+(diff_LRY(2)−diff_LRY(1))−1)=15+(12−6−1)=20. The loop will continue for (n−2) number of time zones. The last two time zones are assigned times using i=i+1, wherein LRt(2*i+3)=LRt(2*i+2)+(diff_LR_Y(diff_LRY(i+1)) and LRt(2*i+4)=LR_tE.

Following termination of the above loops, another ii loop is initiated for which i starts at zero and goes up to length(LRt)/2−1). Time 11 is equated to LRt(2*i+1) and time22 is equated to LRt(2*i+2). If (time22−time 11) is greater than 10, then LimbZoneStatistics is called and the resulting values are stored in LimbZoneStats. LimbZoneStats is set to LimbZoneStatistics(LEFTRIGHT_Y, LEFTRIGHT_GRF, time11, time22). At this point, the if and for loops are ended and the start and end times of the limbZone are stored into TimeZonesLEFTRIGHT.

III. Cows_Separation.m Subroutine

In the cows_separation subroutine, the values of time in msec (time_ms), X and Y coordinates of the left and right limbs (X_LEFT, Y_LEFT, X_RIGHT, and Y_RIGHT), value of moment about the Y axis for left and right plates (ADD_LEFT, ADD_RIGHT), ground reaction force (GRF) for left and right plates (GRF_LEFT, GRF_RIGHT), weight function versus time (WEIGHT), and maximum value of recorded weight (max_weight) are recorded. All these values are calculated by the function named XYGRFPlot and their values are recorded in variable XYGRF_LEFT_RIGHT. The file Y_POS.dat is opened and the stored data read into variable Y_POS. Y_POS is a matrix with 5 columns and its assigned values are as follows (starting with $1^{st}$ and up to $5^{th}$ column): time_ms, LEFT_Y, LEFT_GRF, RIGHT_Y, RIGHT_GRF.

The function TimeZones_LEFTRIGHT is then called with values of LEFT_Y and LEFT_GRF. This function returns the values of start and end times (denoted as L_tS, and L_tE, respectively) of a tested time zone of the left plate.

The data recorded in datafile named LEFTRIGHT_LIMB_STATS.dat is loaded and stored as a variable named L_Limbs. A loop with a counter named yy starts from 1 and goes up to the sum of the total number of limbs encountered on the left plate (cumulative sum (cumsum) of L_Limbs (12,;). If NewCow_TimeOnLeft>0 the yy loop is terminated.

The next few "if statements" check to see if it is the first time the program going through the code. First time checks are different from the rest of the checks. The program checks if the tested timezone contains data of a single limb (L_Limbs(12,:)==1) and whether or not it is the first time through (FHL_Limb==0). If these to conditions are met, the tested limb is a fore and FHL_Limb is set to 1.

Else if the tested timezone contains data of 2 limbs (L_Limb(12,:)==2) and it is the first time through (FHL_Limb==0), the function TwoLimbSeparation is activated and the GRF signatures of the two limbs are decomposed into two GRF signatures of a single limb. These signatures are written into L_Limbs variable. At this point the function LimbSequence_LEFTRIGHT_Check is activated and if it returns a TRUE (value of 10) the loop is terminated. Otherwise, the value returned from LimbSequence_LEFTRIGHT is recorded into variable LimbSequenceCheck and into FHL_Limb.

Else if the tested timezone contains data of 3 limbs (L_Limb(12,:)==3) and it is the first time through (FHL_Limb==0), and the time at which maximum slope of Y position is less than the time at which minimum slope of Y position occurs (L_Limbs(5,:)<L_Limbs(7,:)), then the function ThreeLimbSeparationCase1 is activated and the GRF signatures of the three limbs are decomposed into three GRF signatures of a single limb. These signatures are written into L_Limbs variable. At this point the function LimbSequence_LEFTRIGHT_Check is activated and if it returns a TRUE (value of 10) the loop is terminated. Else the value returned from LimbSequence_LEFTRIGHT is recorded into variable LimbSequenceCheck and into FHL_Limb.

Else if the tested timezone contains data of 3 limbs (L_Limb(12,:)==3) and it is the first time through (FHL_Limb==0), and the time at which maximum slope of Y position is greater than the time at which minimum slope of Y position occurs (L_Limbs(5,:)>L_Limbs(7,:)), the function ThreeLimbSeparationCase2 is activated and the GRF signatures of the three limbs are decomposed into three GRF signatures of a single limb. These signatures are written into L_Limbs variable. At this point the function LimbSequence_LEFTRIGHT_Check is activated and if it returns a TRUE (value of 10) the loop is terminated. Else the value returned from LimbSequence_LEFTRIGHT is recorded into variable LimbSequenceCheck and into FHL_Limb.

Else LimbSequence_LEFTRIGHT_Check is activated and the value of LimbSequenceCheck is tested to be TRUE (LimbSequenceCheck==10). Here the tested zone contains data of a single limb (L_Limbs(12,:)==1 and it is not the first time through the program is executed (FHL_Limb is not 0). A returned TRUE value (LimbSequenceCheck=10) terminates the loop, otherwise FHL_Limb is updated to be the value of LimbSequenceCheck.

If the data in a time zone contains 2 limbs (L_Limbs(12,:)==2) and it is not the first time through the code (FHL_Limb is not 0), TwoLimbSeparation is activated and the GRF signatures of the 2 limbs are decomposed as 2 signatures of a single limb (L_Limbs=Two_Limb_Separation).

Else if the tested timezone contains data of 3 limbs (L_Limb(12,:)==3) and the time at which maximum slope of Y position is less than the time at which minimum slope of Y position occurs (L_Limbs(5,:)<L_Limbs(7,:)), then ThreeLimbSeparationCase1 is activated and the GRF signatures of the three limbs are decomposed into three GRF signatures of a single limb. These signatures are written into L_Limbs variable.

Else if the tested timezone contains data of 3 limbs (L_Limb(12,:)==3) and the time at which maximum slope of Y position is greater than the time at which minimum slope of Y position occurs (L_Limbs(5,:)>L_Limbs(7,:)) ThreeLimbSeparationCase2 is activated and the GRF signatures of the three limbs are decomposed into three GRF signatures of a single limb. These signatures are written into L_Limbs variable.

The function NewCow_TimeOnLEFTRIGHT is activated and the time at which a new cow on the left plate is identified and recorded as NewCowTimeOnLEFT. The entire process listed above is repeated for the right plate and the time at which the records of a new cow is identified on the right plate is recorded as NewCowTimeOnRight.

The maximum between NewCowTimeOnLeft and NewCowTimeOnRight is identified and it is recorded as variable n. Then the records of left and right sides of a single cow are merged. In one aspect, the corresponding loadcell data of the first n records are stored into a variable name firstcow_rawdata with a margin of 20 zeros optionally appended at the end of the record. If newcow_timeOnLeft<newcowtimeOnRight zeros are inserted into the $1^{st}$–$4^{th}$ columns (left plate load cells) of a matrix firstcow_rawdata from entry newcow_timeOnLEFT+1 until newcow_timeOnRIGHT. Else if newcow_timeOnLeft>newcowtimeOnRight zeros are inserted into the $5^{th}$–$8^{th}$ columns (right plate load cells) of a matrix firstcow_rawdata from entry newcow_timeOnRIGHT+1 until newcow_timeOnLEFT. This matrix newcowloadcell is recorded as a separate file and it is named firstcow_rawdata. The recorded variables are plotted on the monitor using function XYGRFPlot.

If NewCowTimeOnLeft or NewCowTimeOnRight is zero, then the variables nextcow_timeonRIGHT and nextcow_timeonLEFT are set to zero. Else nextcow_timeonLEFT=NewCowTimeOnLEFT+10. If newcowTimeonLEFT or newcowTimeonRIGHT is zero, then the variables nextcow_timeonRIGHT and nextcow_timeonLEFT are set to zero. Else nextcow_timeonRIGHT=NewCowTimeOnRight+10. If (nextcow_timeonLEFT<nextcow_timeonRIGHT), then loadcell matrix is padded with zeros at the $5^{th\ to\ the}\ 8^{th}$ columns (right plate) from entry nextcow_timeonLEFT to entry nextcow_timeonRIGHT+10.

Else if (nextcow_timeonLEFT>nextcow_timeonRIGHT) then the loadcell matrix is padded with zero entries at the $1^{st}$ to $4^{th}$ columns from entry nextcow_timeonRIGHT to entry nextcow_timeonLEFT.

If newcow_timeonLEFT and newcow_timeonRIGHT are both greater than zero, then a matrix named newcowloadcell obtains the loadcell value of the remaining animals (i.e., the values of the all the 8 columns of matrix loadcell starting at entry n−20). This newcowloadcell is converted to lb and plotted. At this point the cowseparation function is activated and the process continues until newcowloadcell contains data of only a single cow.

IV. TwoLimbSeparation.m Subroutine

The following variables are passed to the TwoLimbSeparation function: Limb statistics (LR_Limbs), Y position (LEFTRIGHT_Y), GRF (GRF_LEFTRIGHT), moment about Y axis (ADD_LEFTRIGHT), an integer that indicates which of the tested zones are 2 limb zones (kr), and the maximum animal weight (max_weight). The number of rows and columns of the limb statistics are found by calling the Matlab's size function on LR_Limbs, and it is stored into x, and y, respectively.

A yy1 loop is initiated starting at the tested limb zone starting time plus a threshold of 10, ((LR_Limbs(10,:)+10)

up to the limb zone end time minus a threshold of 10 (LR_Limbs(11,;)−10). In this loop the difference between a running window of 5 units wide and the Y position vector is evaluated and, in case it is greater or equal to 3, the loop breaks and the yy1 value at which it happens first is recorded.

A yy2 loop is initiated starting at the end time of the tested limb zone minus a threshold of 10 ((LR_Limbs(11,;)−10) going back to the starting time of the limb zone plus a threshold of 10 ((LR_Limbs(10,;)+10). In this loop the difference between a running window of 5 unit wide the of Y position vector is evaluated and in case the absolute value of it is greater or equal to 3 the loop breaks and the yy2 value at which it happens first is recorded.

To determine separation of forces, Ym1 is assigned the mean value of the Y position vector starting at the starting time of the tested limb zone plus a threshold of 10 (LR_Limbs(10,;)+10) up to yy1. Ym2 is assigned the mean value of the Y position vector starting at the end time of the of the tested limb zone minus a threshold of 10 (LR_Limbs(11,;)−10) down to yy2.

A mm loop is initiated from starting time (LR_Limbs (10,;) to end time (LR_Limbs(11,;) of the tested limb zone. Kramer's rule is utilized for solving two simultaneous equilibrium equations and from a GRF signature of two limbs (GRF_LEFTRIGHT) two separate GRF signatures of two singulated limbs are evaluated (GRF_LRFTRIGHT_yy1 and GRF_LRFTRIGHT_yy2. One example of such coding would have, for mm equal to LR_Limbs (10, kr):LR_Limbs(11,kr), D1(mm) is equal to det([GRF_LEFTRIGHT(mm) 1; ADD_LEFTRIGHT(mm) Ym2]) and D2(mm) is equal to det([1 GRF_LEFTRIGHT(mm); Ym1 ADD_LEFTRIGHT(mm)]), where Ym1 is equal to mean (LEFTRIGHT_Y((LR_Limbs(10,kr)+10):yy1)) and Ym2 is equal to mean(LEFTRIGHT_Y((LR_Limbs(11,kr)−10) :−1:yy2)). The matrix D is equal to det([1 1; Ym1 Ym2]). Correspondingly, the decomposed GRF_LEFTRIGHT_yy1 is equal to D1./D and GRF_LEFTRIGHT_yy2 is equal to D2./D.

The time for which GRF_LEFTRIGHT_yy1 is maximum and greater than 100 is recorded into LEFTRIGHT_yy1_t1. The time for which GRF_LEFTRIGHT_yy2 is minimum and greater than 100 is recorded into LEFTRIGHT_yy2_t2.

In the shifting of limb zone statistics, a reverse kk loop starts at the number of columns of the limb zone statistics matrix (y) and ends at the current index of the tested limb zone (kr). The kk-th tested column of limb statistics matrix (LR_Limbs(;,kk)) is copied into the (kk+1)-th column. The starting time and ending time of the second (separated) limb are recorded as time11 and time22, respectively. The limb statistics of the separated second limb zone are calculated and stored into LimbZoneStats variable at the (kr+1)-th column of LR_Limbs matrix. The starting time and ending time of the first (separated) limb are recorded as time11 and time22, respectively. The limb statistics of the separated first limb zone are calculated and stored into LimbZoneStats variable at the (kr)-th column of LR_Limbs matrix.

The matrix Two_Limb_Separation is updated.

V. ThreeLimbSeparationCase1.m Subroutine

The following variables are passed to the ThreeLimb-Seprationcase1 function: Limb statistics (LR_Limbs), Y position (LEFTRIGHT_Y), row loadcell values of GRF (LEFTRIGHT_GRF), normalized GRF (GRF_LEFTRIGHT), moment about Y axis (ADD_LEFTRIGHT), an integer that indicates which of the tested zones are 3 limb zones (kr), and the maximum animal weight (max_weight). The number of rows and columns of the limb statistics are found by calling the Matlab's size function on LR_Limbs, and it is stored into x, and y, respectively.

A yy1 loop is initiated starting at the tested limb zone starting time plus a threshold of 2, ((LR_Limbs(10,;)+2) up to the time at which minimum y position slope occurs in the tested limb zone minus a threshold of 2 (LR_Limbs(7,;)−2). In this loop the absolute value of the difference between a running window of 2 units wide the Y position vector is evaluated and in case it is less than 2 the loop breaks and the yy1 value at which it happens first is recorded.

A yy2 loop is initiated starting at the time at which minimum y position slope occurs in the tested limb zone minus a threshold of 2 units ((LR_Limbs(7,;)−2) going backward to the starting time of the limb zone plus a threshold of 2 ((LR_Limbs(10,;)+2). In this loop the absolute value of the difference between a running window of 2 unit wide of the Y position vector is evaluated and in case it is less than 2 the loop breaks and the yy2 value at which it happens first is recorded.

To determine separation of forces, Ym1 and Ym2 are assigned the Y position values at times yy1 and yy2, respectively. A mm loop is initiated from starting time (LR_Limbs(10,;) to end time (LR_Limbs(11,;) of the tested limb zone. Kramer's rule is utilized for solving two simultaneous equilibrium equations and from a GRF signature of two limbs (GRF_LEFTRIGHT) two separate GRF signatures of two singulated limbs are evaluated (GRF_LRFTRIGHT_yy1 and GRF_LRFTRIGHT_yy2. The time for which GRF_LEFTRIGHT_yy1 is maximum and greater than 100 is recorded into LEFTRIGHT_yy1_t1. The time for which GRF_LEFTRIGHT_yy2 is minimum and greater than 100 is recorded into LEFTRIGHT_yy2 t2.

In the shifting of limb zone statistics, a reverse kk loop starts at the number of columns of the limb zone startistics matrix (y) and ends at the current index of the tested limb zone (kr). The kk-th tested column of limb statistics matrix (LR_Limbs(;,kk)) is copied twice, once into the (kk+1)-th column and a second time into the (kk+2)-th column.

In the recalculation of limb zone statistics for the first part of three limb position, The starting time and ending time of the first limb are recorded as time11 and time22, respectively. The limb statistics of the separated first limb zone are calculated and stored into LimbZoneStats variable at the (kr)-th column of LR_Limbs matrix. The starting time and ending time of the third limb are recorded as time11 and time22, respectively. In the recalculation of limb zone statistics for the second part of three limb position, the starting time and ending time of the second limb in this record of 3 limbs are time11 and time22, respectively. The limb statistics of the separated second limb zone are calculated and stored into LimbZoneStats variable at the (kr+1)-th column of LR_Limbs matrix. In the recalculation of limb zone statistics for the first part of three limb position, the limb statistics of the separated third limb zone are calculated and stored into LimbZoneStats variable at the (kr+2)-th column of LR_Limbs matrix.

The matrix Three_Limb_Separation is updated.

VI. ThreeLimbSeparationCase2.m Subroutine

The following variables are passed to the ThreeLimb-Seprationcase2 function: Limb statistics (LR_Limbs), Y position (LEFTRIGHT_Y), row loadcell values of GRF (LEFTRIGHT_GRF), normalized GRF (GRF_LEFTRIGHT), moment about Y axis (ADD_LEFTRIGHT), an integer that indicates which of the tested zones are 3 limb zones (kr), and the maximum animal weight (max_weight). The number of rows and columns of the limb statistics are found by calling the Matlab's size function on LR_Limbs, and it is stored into x, and y, respectively.

A yy1 loop is initiated starting at the tested limb zone starting at time the time at which minimum y position slope occurs plus a threshold of 2 ((LR_Limbs(7,:)+2) up to the end time of the limb zone minus a threshold of 2 (LR_Limbs(11,:)−2). In this loop the absolute value of the difference between a running window of 2 units wide the Y position vector is evaluated and in case it is less than 2 the loop breaks and the yy1 value at which it happens first is recorded.

A yy2 loop is initiated starting at the end time of the tested limb zone minus a threshold of 2 units ((LR_Limbs(11,:)−2) going backward to the time at which minimum y position slope occurs plus a threshold of 2 ((LR_Limbs(7,:)+2). In this loop the absolute value of the difference between a running window of 2 unit wide of the Y position vector is evaluated and in case it is less than 2 the loop breaks and the yy2 value at which it happens first is recorded.

To determine separation of forces, Ym1 and Ym2 are assigned the Y position values at times yy1 and yy2, respectively. A mm loop is initiated from starting time (LR_Limbs(10,:) to end time (LR_Limbs(11,:) of the tested limb zone. Kramer's rule is utilized for solving two simultaneous equilibrium equations and from a GRF signature of two limbs (GRF_LEFTRIGHT) two separate GRF signatures of two singulated limbs are evaluated (GRF_LRFTRIGHT_yy1 and GRF_LRFTRIGHT_yy2. The time for which GRF_LEFTRIGHT_yy1 is maximum and greater than 100 is recorded into LEFTRIGHT_yy1_t1. The time for which GRF_LEFTRIGHT_yy2 is minimum and greater than 100 is recorded into LEFTRIGHT_yy2_t2.

In the shifting of limb zone statistics, a reverse kk loop starts at the number of columns of the limb zone statistics matrix (y) and ends at the current index of the tested limb zone (kr). The kk-th tested column of limb statistics matrix (LR_Limbs(:,kk)) is copied twice. Once into the (kk+1)-th column and the second time into the (kk+2)-th column. The starting time and ending time of the second limb in this record of 3 limbs are time11 and time22, respectively.

The limb statistics of the separated first limb zone are calculated and stored into LimbZoneStats variable at the (kr)-th column of LR_Limbs matrix. The starting time and ending time of the first limb are recorded as time11 and time22, respectively. The limb statistics of the separated third limb zone are calculated and stored into LimbZoneStats variable at the (kr+2)-th column of LR_Limbs matrix. The starting time and ending time of the third limb are recorded as time11 and time22, respectively. The limb statistics of the separated second limb zone are calculated and stored into LimbZoneStats variable at the (kr+1)-th column of LR_Limbs matrix.

The matrix Three_Limb_Separation is updated.

VII. LimbZoneStatistics.m Subroutine

The following variables are passed to the function LimbZoneStatistics: Y_position vector (LIMB_Y 1), GRF vector for the tested limb (LIMB_GRF1), start and end times of the tested limb zone (time1 and time2, respectively).

Then, variables that are internal to this function are initialized, including max_Rt_slope=−1000000; min_Rt_slope=1000000; pos_delta_slope_counter=0; neg_delta_slope_counter=0; delta_grfslope_counter=0; time_min_slope=1000000; and time_max_slope=−1000000. If(time2−time1)>30 calculate the values of average Y position (Y_mean), maximum Y position value (Y_max), and minimum Y position value (Y_min). In these calculations the margin thresholds of the Y position vector is set to 10.

Next, the maximum or peak and average ground reaction force (GRF) between (time1+10) and (time2−10) are determined and stored in RGRF_max and R_AGRF, respectively. R_AGRF is determined first by defining RCUMGRF=(cumsum(LIMB_GRF 1 ((time1+10): (time 2−10)))), wherein R_IMPULSE=maxRCUMGRF)*0.01 and R_stancetime=(abs((time1+10)−(time2−10)))*0.01. R_AGRF is then set to the ratio of (R_IMPULSE)/(R_stancetime).

To calculate the maximum and minimum slopes and respective times, initiate a loop j running from (time1+10) up to (time2−20) and calculate the slope of running window with width 10 of the Y position values (Rt_slope). The minimum and maximum values of the slope and the times at which these minimum and maximum values occur are calculated (min_Rt_slope, and time_min_slope, max_Rt_slope, and time_max_slope, respectively).

If (Rt_slope>2), pos_delta_slope_counter is incremented up by 1 unit. If (Rt_slope<−2), neg_delta_slope_counter is incremented up by 1 unit.

Initiating a jjjj loop starting from time1 up to (time2−2). In this loop, we calculate the GRF slope for a running window with width of 2 units. If the product of two successive GRF slope values are negative then the value of delta_grfslope_counter is incremented by 1.

In case the difference between time2 and time1 is less than 30 then the values of average Y position (Y_mean), maximum Y position value (Y_max), and minimum Y position value (Y_min) are calculated with a margin threshold of 5. For example, Y_mean is calculated as abs(mean(LIMB_Y1((time1+5): (time 2−5)))).

The maximum or peak and average GRFs for the limb zones are then calculated between (time1+5) and (time2−5) and stored in RGRF_max and R_AGRF, respectively. The calculation of R_AGRF is similar to that noted above.

The maximum and minimum slopes and respective times are then determined. A j loop running from (time1+5) up to (time2−10) calculates the slope of running window with width 5 of the Y position values (Rt_slope). The minimum and maximum values of the slope and the times at which these minimum and maximum values occur are calculated (min_Rt_slope, and time_min_slope, max_Rt_slope, and time_max_slope, respectively).

If (Rt_slope>2), pos_delta_slope_counter is incremented up by 1 unit. If (Rt_slope<−2), neg_delta_slope_counter is incremented up by 1 unit.

A jjjj loop is initiated starting from time1 up to (time2−2). In this loop the GRF slope is calculated for a running window with width of 2 units. For example, Rt_GRFslope (jjjj)=(((LIMB_GRF1(jjjj+2)−LIMB_GRF1(jjjj)))). If the product of two successive GRF slope values are negative than the value of delta_grfslope_counter is incremented by 1.

In the following 'if-else' statements the code determines if a tested limbzone is a one, two, or three limbzone.

If any of the following sets of conditions are satisfied, then the number of limbs in the zone is one (IRt_Limb=1): ((Y_max−Y_min)<6 and (Y_mean−Y_min)<6 and max_Rt_slope<5 and min_Rt_slope>−5)); or ((delta_grfslope_counter=1) and (max_Rt_slope<5) and (min_Rt_slope>−5)); or ((delta_grfslope_counter=1) and (max_Rt_slope>=5) and ((time_max_slope−time1)<20) and (min_Rt_slope>−5)); or ((delta_grfslope_counter=1) and (max_Rt_slope>=5) and ((time2−time_max_slope)

<20) and (min_Rt_slope>−5)); or ((delta_grfslope_counter=1) and (min_Rt_slope<=−5) and ((time2−time_min_slope)<20) and (max_Rt_slope<5)); or ((delta_grfslope_counter=1) and (min_Rt_slope<=−5) and ((time_min_slope−time1)<20) and (max_Rt_slope<5))).

Elseif ((Y_max−Y_mean<6) and (Y_mean−Y_min<6) and (pos_delta_slope_counter<0.09*(time2−time1)) and (neg_delta_slope_counter<0.09*(time2−time1))), then the number of limbs in this zone is 1 (IRt_Limb=1).

Elseif ((Y_max−Y_mean>6) and (Y_mean−Y_min>6) and (max_Rt_slope>5) and (min_Rt_slope<−5) and (pos_delta_slope_counter>0.09*(time 2−time1)) and (neg_delta_slope_counter>0.09*(time2−time1))) then the number of limbs in this zone is 3 (IRt_Limb=3).

Else the number of limbs is 2 (IRt_Limb=2).

The LimbZoneStats vector is updated with the calculated values of Y_mean, Y_max, Y_min, abs(max_Rt_slope), time_max_slope, min_Rt_slope, time_min_slope, RGRF_max, R_AGRF, time1, time2, IRt_Limb, pos_delta_slope_counter, neg_delta_slope_counter, IRt_Limb, and delta_grfslope_counter.

VIII. LimbZoneStatisticsfortwolimb1.m Subroutine

The variables Y_position vector (LIMB_Y1), GRF vector for the tested limb (LIMB_GRF1), Y_position for the separated limb in a two limb case (Ym), start and end times of the tested limb zone (time1 and time2, respectively) are passed to the function LimbZoneStatisticsfortwolimb 1. Variables internal to this function are initialized.

The peak and average GRFs between (time1+10) and (time2−10) are calculated and stored in RGRF_max and R_AGRF, respectively.

A loop j running from (time1+10) up to (time2−20) is initiated and the slope of running window with width 10 of the Y position values (Rt_slope) calculated. The minimum and maximum values of the slope and the times at which these minimum and maximum values occur are calculated (min_Rt_slope, and time_min_slope, max_Rt_slope, and time_max_slope, respectively).

If (Rt_slope>2), pos_delta_slope_counter is incremented up by 1 unit. If (Rt_slope<−2), neg_delta_slope_counter is incremented up by 1 unit.

A jjjj loop is initiated starting from time1 up to (time2−2). In this loop, the GRF slope is calculated for a running window with width of 2 units. If the product of two successive GRF slope values are negative then the value of delta_grfslope_counter is incremented by 1.

If the difference between time2 and time1 is less than 30, then the values of average Y position (Y_mean), maximum Y position value (Y_max), and minimum Y position value (Y_min) are calculated with a margin threshold of 5.

The peak and average ground reaction force(GRF) between (time1+5) and (time 2−5) are calculated and stored in RGRF_max and R_AGRF, respectively.

A loop j running from (time1+5) up to (time2−10) is initiated and the slope of running window with width 5 of the Y position values (Rt_slope) is calculated. The minimum and maximum values of the slope and the times at which these minimum and maximum values occur are calculated (min_Rt_slope, and time_min_slope, max_Rt_slope, and time_max_slope, respectively).

If (Rt_slope>2), pos_delta_slope_counter is incremented up by 1 unit. If (Rt_slope<−2), neg_delta_slope_counter is incremented up by 1 unit.

A jjjj loop starting from time1 up to (time2−2) is initiated. In this loop the GRF slope for a running window with width of 2 units is calculated and, if the product of two successive GRF slope values are negative, then the value of delta_grfslope_counter is incremented by 1.

At the end of the routine, the limbs are separated, so it is assured that the tested limb zone are single limb zones and the variable IRt_Limb is assigned value 1 (IRt_Limb=1).

The LimbZoneStats vector is updated with the calculated values of Y_mean, Y_max, Y_min, abs(max_Rt_slope), time_max_slope, min_Rt_slope, time_min_slope, RGRF_max, R_AGRF, time1, time2, IRt_Limb, pos_delta_slope_counter, neg_delta_slope_counter, IRt_TwoLlimb, and delta_grfslope_counter.

IX. NewCow_LEFTRIGHT_Check.m Subroutine

The following variables are passed to the function NewCow_LEFTRIGHT_Check: Fore/hind limb sequence (FHLR_Limb (1 for fore, −1 for hind, 100 when the limb at the front end of the plate (within 5 inches of the front end, and −100 when the limb is at the rear end of the plate (within 5 inches of the end)), matrix of limb zone statistics (LR_Limbs). Variables internal to this subroutine are being initialized.

A loop ii is initiated from 1 to (length of the matrix FHLR_Limb−1).

If any one of the following sets of conditions are satisfied, then the tested limb zone belongs to a new cow (New_Cow_LEFTRIGHT=1): (1) the limb one before current limb is hind (FHLR_Limb(ii)=−1) and the current limb is fore (FHLR_Limb(ii+1)=1) and the average Y_position of the limb before current is greater than the average Y_position of the current limb (LR_Limbs(1,ii)>LR_Limbs(1,(ii+1))); or (2) the limb before the current limb is hind (FHLR_Limb(ii)=−1) and the current limb is fore (FHLR_Limb(ii+1)=1) and the the difference between the start time of the current limb and the end time of the one before current limb is greater than 0.5 sec (LR_Limbs(10,(ii+1))−LR_Limbs(11,(ii))>50); or (3) the number of limbs in the tested zone is 1 (LR_Limbs(12, (ii+1))=1) and the limb before current is within 5 inches of the beginning of the plate (FHLR_Limb(ii)=100) and the difference between the average Y_Position of the limb before current and the average Y position of the current limb is greater than 15 (LR_Limbs(1,(ii)))−(LR_Limbs(1,(ii+1))))>15); or (4) the limb before current is hind (FHLR_Limb(ii)=−1) and current limb is within 1 inches from the front end of the plate (FHLR_Limb(ii+1)=−100) and the average Y_position of the limb before current limb is greater than average Y_Position of the current limb (LR_Limbs(1,ii)>LR_Limbs(1,(ii+1)).

The starting time of the new cow is recorded in NewCow_TimeOnLEFTRIGHT.

X. LimbSequence_LEFTRIGHT_Check.m Subroutine

The variables passed to the functionLimbSequence_LEFTRIGHT_Check include Fore/hind limb sequence (FHLR_Limb (1 for fore, −1 for hind, −100 when the limb at the front end of the plate (within 1 inch of the front end), and 100 when the limb is at the rear end of the plate (within 6 inches of the end)), matrix of limb zone statistics (LR_Limbs), and a running index of the tested limb zone (kkr). Variables internal to the subroutine are initialized.

The subroutine identifies if the tested limbzone is of fore or hind limb and determines which of four different cases are applicable, as described below.

In a subroutine denoted as "Case 0", the following conditions are evaluated. If the tested limbzone belongs to a single limb (LR_Limbs(12, kkr)=1) and it is the first limb in the sequence that is tested (FHLR_Limb=0) then the limb is fore and FHLR_Limb(kkr) is assigned a 1 value. Elseif the tested limb zone is of a single limb (LR_Limbs(12, kkr)=1) and the average Y_position is greater than 72 inches end of the plate (LR_Limbs(1,kkr)>72) then FHLR_Limb(kkr) is assigned a 100 value (FHLR_Limb(kkr)=100). Elseif tested limb zone is of a single limb ((LR_Limbs(12, kkr)=1) and the average Y_position is less than 1 inch the front end of the plate (LR_Limbs(1,kkr)<1) then FHLR is assigned−100 value FHLR_Limb(kkr)=−100.

In a subroutine denoted as "Case 1", the following additional conditions are evaluated. If (1) the tested limbzone is of a single limb (LR_Limbs(12, kkr)=1) and the limb before the tested limb is fore (FHLR_Limb(kkr−1)=1) and the limb before the tested limb is not on the end of the plate (FHLR_Limb(kkr−1)~=100) and the limb before the tested limb is not on the beginning of the plate (FHLR_Limb(kkr−1)~=(−100)) and the AGRF of the previous limb is greater than or equal to 1.04*AGRF of tested limb (LR_Limbs(9, (kkr−1))>=(LR_Limbs(9, (kkr))*1.04)) and the difference between the average Y_Position of the previous and current limb zones is less than 5 ((LR_Limbs(1,kkr)−LR_Limbs(1,(kkr−1)))<5)); or (2) the tested limbzone is of a single limb (LR_Limbs(12, kkr)=1) and the limb before the tested limb is fore (FHLR_Limb(kkr−1)=1) and the difference between the average Y_Position of the previous and current limb zones is less than 10 ((LR_Limbs(1,kkr)−LR_Limbs(1,(kkr−1)))<10)); or (3) the tested limbzone is of a single limb (LR_Limbs(12, kkr)=1) and the limb before the tested limb is fore (FHLR_Limb(kkr−1)=1) and the PGRF of the previous limb is greater 1.15*PGRF of current limb (LR_Limbs(8,(kkr−1))−LR_Limbs(8,(kkr)))>0.15*(LR_Limbs(8,(kkr)); or (4) the tested limbzone is of a single limb (LR_Limbs(12, kkr)=1) and the limb before the tested limb is fore (FHLR_Limb(kkr−1)=1) and the GRF slope counter of the current zone is greater than 3 (LR_Limbs(16, kkr)>=3), then the tested limb is hind (FHLR_Limb(kkr)=−1).

In a subroutine denoted as "Case 2", the following additional conditions are evaluated. If the tested limbzone is of a single limb (LR_Limbs(12, kkr)=1) and the limb before the tested limb is fore (FHLR_Limb(kkr−1)=1) and the limb before the tested limb is not on the end of the plate (FHLR_Limb(kkr−1)~=100) and the limb before the tested limb is not on the beginning of the plate (FHLR_Limb(kkr−1)~=(−100)) and the difference between the average Y_Position of the previous and current limb zones is greater than or equal to 5 ((LR_Limbs(1,kkr)−LR_Limbs(1,(kkr−1)))>=5)), then the tested limbzone is a fore.

In a subroutine denoted as "Case 3", the following additional conditions are evaluated. If (1) the tested limbzone is of a single limb (LR_Limbs(12, kkr)=1) and the limb before the tested limb is hind (FHLR_Limb(kkr−1)=0) and the limb before the tested limb is not on the end of the plate (FHLR_Limb(kkr−1)~=100) and the limb before the tested limb is not on the beginning of the plate (FHLR_Limb(kkr−1)~=(−100)) and the AGRF of the previous limb is greater than 1.05*AGRF of tested limb (LR_Limbs(9, (kkr−1))>(LR_Limbs(9, (kkr))*1.05)) and the difference between the average Y_Position of the previous and current limb zones is less than or equal to 0 ((LR_Limbs(1,kkr)−LR_Limbs(1,(kkr−1)))=<0)); or (2) the tested limbzone is of a single limb (LR_Limbs(12, kkr)=1) and the limb before the tested limb is hind (FHLR_Limb(kkr−1)=0) and AGRF of previous limb is greater than 1.02*AGRF of current limb (LR_Limbs(9,(kkr−1))>(LR_Limbs(9,(kkr))*1.02)) and the difference between average Y_position of current and previous limbs is less than or equal to −15 (LR_Limbs(1,kkr)−LR_Limbs(1, kkr−1)<=−15); or (3) the tested limbzone is of a single limb (LR_Limbs(12, kkr)=1) and the limb before the tested limb is hind (FHLR_Limb(kkr−1)=0) and AGRF of previous limb is greater than 1.1*AGRF of current limb (LR_Limbs(9, (kkr−1))>(LR_Limbs(9, (kkr))*1.1)) or (4) the tested limbzone is of a single limb (LR_Limbs(12, kkr)=1) and the limb before the tested limb is hind (FHLR_Limb(kkr−1)=0) and PGRF of previous limb is greater than 1.1*PGRF of current limb (LR_Limbs(8, (kkr−1))>(LR_Limbs(8, (kkr))*1.1)), then the tested limb zone is fore (FHLR_Limb(kkr)=1).

In a subroutine denoted as "Case 4", the following additional conditions are evaluated. If (1) the tested limbzone is of a single limb (LR_Limbs(12, kkr)=1) and the limb before the tested limb is hind (FHLR_Limb(kkr−1)=0) and the limb before the tested limb is not on the end of the plate (FHLR_Limb(kkr−1)~=100) and the limb before the tested limb is not on the beginning of the plate (FHLR_Limb(kkr−1)~=±(−100)) and the AGRF of the previous limb is less than or equal to 1.05*AGRF of tested limb (LR_Limbs(9, (kkr−1))<=(LR_Limbs(9, (kkr))*1.05)) and the difference between the average Y_Position of the previous and current limb zones is greater than 0 ((LR_Limbs(1,kkr)−LR_Limbs(1,(kkr−1)))>0)); or (2) the tested limbzone is of a single limb (LR_Limbs(12, kkr)=1) and the limb before the tested limb is hind (FHLR_Limb(kkr−1)=0) and AGRF of previous limb is greater than or equal to 1.05*AGRF of current limb (LR_Limbs(9, (kkr−1))>=(LR_Limbs(9, (kkr))*1.05)) and the difference between average Y_position of current and previous limbs is greater than or equal to 40 (LR_Limbs(1, kkr)−LR_Limbs(1, kkr−1)>=−40); or (3) the tested limbzone is of a single limb (LR_Limbs(12, kkr)=1) and the limb before the tested limb is hind (FHLR_Limb(kkr−1)=0) and and the difference between average Y_position of current and previous limbs is greater than or equal to 40 (LR_Limbs(1, kkr)−LR_Limbs(1, kkr−1)>=−40), then the tested limb is hind (FHLR_Limb(kkr)=−1).

The limb sequence is passed to NewCow_LEFTRIGHT_Check function. This function checks if the sequence belongs to two cows or a single cow. If it is a single cow nothing is done, else the variable LimbSequenceCheck is assigned value of 10 and the loop is terminated.

XI. XYGRFPlot.m Subroutine

In the optional plotting subroutine, the following variables are passed to the function XYGRFPlot: time (time_ms), load cell data in lbs (LC1, LC2, . . . , LC8), cow number (cow_num_str), date (date_str), time (time_str).

The weight of the animal is calculated by summing the 8 loadcells and taking the maximum value of the weight vector. Weight versus time is plotted, wherein the size of the time vector is determined using a length command.

The moment about the Y axis for the right plate is calculated and stored as ADD_RIGHT. The sum of the forces on the right plate is stored as GRF_RIGHT.

A loop i from 1 to the length of the time vector is initiated. If GRF_RIGHT>30 the X position is calculated and stored as X_RIGHT1. Else X_RIGHT1=0.

The moment about the X axis for the right plate is calculated and stored as ADD_RIGHT. The sum of the forces on the right plate is stored as GRF_RIGHT.

A loop i from 1 to the length of the time vector is initiated. If GRF_RIGHT>30 the Y position is calculated and stored as Y_RIGHT1. Else Y_RIGHT1=0.

The sum of the forces for right plate is calculated and divided by the maximum weight of the weight vector. This variable is stored as NGRF_RIGHT.

A loop i from 1 to the length of the time vector is initiated. If NGRF_RIGHT<0 then NGRF_RIGHT=0.

The procedure listed above for calculating X_Position, Y_Position, and normalized GRF for limbs on right plate is repeated for left plate.

These calculated variables are plotted as a function of time using a subplot command and are stored in XYGRF_LEFTRIGHT matrix.

The above disclosed concepts may be utilized in combination with any conventional computer system comprising, for example, a bus or other communication mechanism for communicating information, a processor or processors coupled with bus for processing information, and a main memory such as a random access memory (RAM) or other dynamic storage device coupled to the bus for storing information and instructions to be executed by processor. The main memory may be used for storing temporary variables or other intermediate information during execution of instructions to be executed by the processor(s). Such computer system may further include a read only memory (ROM) or other static storage device coupled to the bus for storing static information and instructions for the processor (s). A storage device, such as a magnetic disk or optical disk, may be provided and coupled to the bus for storing information and instructions.

The computer system may be coupled via the bus to a display device for displaying information to a computer user. One or more input devices (keyboard, touch screen, cursor control, mouse, a trackball, cursor direction keys, microphone, etc.) may be coupled to the bus for communicating information and command selections to the processor (s).

The computer system processes data obtained by the various data input means. The pertinent programs and executable code or instruction sets are preferably contained in main memory and are selectively accessed and executed in response to the processor(s), which execute one or more sequences of one or more instructions contained in the main memory. Such instructions may be read into main memory from another computer-readable medium, such as a storage device. One or more processors in a multi-processing arrangement may also be employed to execute the sequences of instructions contained in main memory.

The instructions may be provided in any number of forms such as source code, assembly code, object code, machine language, compressed or encrypted versions of the foregoing, and any and all equivalents thereof. "Computer-readable medium" refers to any medium that participates in providing instructions to the processor(s) for execution and "program product" refers to such a computer-readable medium bearing a computer-executable program. The computer usable medium may be referred to as "bearing" the instructions, which encompass all ways in which instructions are associated with a computer usable medium.

Computer-readable mediums include, but are not limited to, non-volatile media, volatile media, and transmission media. Non-volatile media include, for example, optical or magnetic disks, such as storage device. Volatile media include dynamic memory, such as main memory. Transmission media include coaxial cables, copper wire and fiber optics, including the wires that comprise bus. Transmission media may comprise acoustic or light waves, such as those generated during radio frequency (RF) and infrared (IR) data communications. Common forms of computer-readable media include, for example, a floppy disk, a flexible disk, hard disk, magnetic tape, any other magnetic medium, a CD-ROM, DVD, any other optical medium, punch cards, paper tape, any other physical medium with patterns of holes, a RAM, a PROM, and EPROM, a FLASH-EPROM, any other memory chip or cartridge, a carrier wave as described hereinafter, or any other medium from which a computer can read.

Various forms of computer readable media may be involved in carrying one or more sequences of one or more instructions to processor for execution. For example, the instructions may initially be borne on a magnetic disk of a remote computer. The remote computer can load the instructions into its dynamic memory and send the instructions over a telephone line using a modem. A modem local to computer system can receive the data on the telephone line and use an infrared transmitter to convert the data to an infrared signal. An infrared detector coupled to bus can receive the data carried in the infrared signal and place the data on bus. Bus carries the data to main memory, from which processor retrieves and executes the instructions. The instructions received by main memory may optionally be stored on storage device either before or after execution by processor.

The computer system may also include a communication interface coupled to the bus to provide a two-way data communication coupling to a network link connected to a local network. For example, communication interface may be an integrated services digital network (ISDN) card or a modem to provide a data communication connection to a corresponding type of telephone line. As another example, communication interface may be a local area network (LAN) card to provide a data communication connection to a compatible LAN. Wireless links may also be implemented. In any such implementation, communication interface sends and receives electrical, electromagnetic or optical signals that carry digital data streams representing various types of information.

Network link typically provides data communication through one or more networks to other data devices. For example, network link may provide a connection through local network to a host computer or to data equipment operated by an Internet Service Provider (ISP). ISP in turn provides data communication services through the world-wide packet data communication network, now commonly referred to as the "Internet". Local network and Internet both use electrical, electromagnetic or optical signals that carry digital data streams. The signals through the various networks and the signals on a network link and through a communication interface, which carry the digital data to and from a computer system, are exemplary forms of carrier waves transporting the information. Thus the processing required by method of the invention described by way of example herein may be implemented on a local computer utilizing storage device or may be implemented, for example, on a LAN or over the internet.

The computer system can send messages and receive data, including program code, through the network(s), network link, and communication interface. In the Internet example, a server might transmit a requested code for an application program through Internet, ISP, local network and a communication interface. The received code may be executed by processor(s) as it is received, and/or stored in storage device, or other non-volatile storage for later execution. In this manner, computer system may obtain application code in the form of a carrier wave.

While the present disclosure sets forth a description of a practical and preferred embodiment, it is understood that the invention is not limited to the disclosed embodiment, but on the contrary, is intended to cover various modifications and equivalent arrangements included within the spirit and scope of the appended claims. The instruction set may be written on any computer readable medium and may be executed on any processor(s) adapted to read said computer readable medium. Moreover, the instruction set noted above takes into consideration various physical variables that are particularly relevant to the illustrated example of bovines. The physical attributes and dynamic characteristics of the subject animals (e.g., bovines) provide unique information which may be used in accord with the invention to discriminate, for example, between a fore limb and a hind limb. For example, the difference between a peak front GRF and a peak rear GRF is about 10–15%, with the hind peak being lower than the fore limb. The hind force signature also has two or three valleys or peaks, with two or three points of inflection in the curve, whereas the fore limbs typically only have one peak. These and other factors, embodied in the above instructions, provide means to reduce the number of unknown variables and permit identification of the events represented in the force traces and deconstruction thereof. Similar or dissimilar factors may be endemic to other types of animals and may be utilized to the same end in accord with the invention.

Accordingly, it is to be understood that the invention, only an example of which is provided herein, is capable of other different embodiments and its several details are capable of modifications in various obvious respects, all without departing from the concepts disclosed herein. The appended figures and description are to be regarded as illustrative in nature, and not as restrictive.

What is claimed is:

1. A computer readable medium bearing instructions for singulating the limbs of a plurality of animals traversing an instrumented force-sensing floor, said instructions being arranged to cause one or more processors upon execution thereof to perform the steps of:
    (a) obtaining a data file comprising positional data and ground reaction force data for said plurality of animals traversing an instrumented force-sensing floor;
    (b) dividing the positional data into a plurality of time zones, each time zone having a start time and an end time;
    (c) determining whether each of said time zones represents positional data and ground reaction force data for a single limb or for multiple limbs;
    (d) singulating multiple limb time zones into a plurality of separate single limb time zones;
    (e) identifying each limb in each time zone as a fore limb or a hind limb and a left limb or a right limb;
    (f) associating each identified fore and hind limb with a respective one of said plurality of animals.

2. A computer readable medium bearing instructions for singulating the limbs of a plurality of animals traversing an instrumented force-sensing floor according to claim 1, wherein step (d) comprises singulating multiple limb time zones via induction into a plurality of separate single limb time zones.

3. A computer readable medium bearing instructions for singulating the limbs of a plurality of animals traversing an instrumented force-sensing floor according to claim 2,
    wherein the instructions arranged to cause one or more processors upon execution thereof to perform step (a) further comprises an instruction or instructions arranged to obtain identification data comprising at least one of time data for data recordation, file numbers, animal tag numbers, and animal identification numbers, and
    wherein the instructions arranged to cause one or more processors upon execution thereof to perform step (a) further comprises an instruction or instructions arranged to calculate a number of animals recorded in each file.

4. A computer readable medium bearing instructions for singulating the limbs of a plurality of animals traversing an instrumented force-sensing floor according to claim 3, wherein the instructions arranged to cause one or more processors upon execution thereof to perform step (b) further comprises an instruction or instructions arranged to find a first vector of indices for which a Y-position of a right limb or a left limb is greater than zero and a second vector of indices for which a Y-position of a right limb or a left limb is greater than one and to utilize at least one of said first vector of indices and said second vector of indices to determine said plurality of time zones.

5. A computer readable medium bearing instructions for singulating the limbs of a plurality of animals traversing an instrumented force-sensing floor according to claim 4, wherein the instructions arranged to cause one or more processors upon execution thereof to perform step (c) further comprises an instruction or instructions arranged to determine a maximum and an average ground reaction force between a start time of a tested limb time zone and an end time of a tested limb time zone if the difference between the start time and the end time is greater than about 30 seconds, and to store said maximum and said average ground reaction force.

6. A computer readable medium bearing instructions for singulating the limbs of a plurality of animals traversing an instrumented force-sensing floor according to claim 5, wherein the instructions arranged to cause one or more processors upon execution thereof to perform step (c) further comprises an instruction or instructions arranged to determine said average ground reaction force by calculating a ratio of an impulse variable over a stancetime variable, said impulse variable calculated by applying a multiplier to a ground reaction force curve area defined between said start time of a tested limb time zone and said end time of a tested limb time zone, and said stancetime variable calculated as the difference in time between said start time of a tested limb time zone and said end time of a tested limb time zone.

7. A computer readable medium bearing instructions for singulating the limbs of a plurality of animals traversing an instrumented force-sensing floor according to claim 6, wherein the instructions arranged to cause one or more processors upon execution thereof to perform step (c) further comprises an instruction or instructions arranged to calculate a slope of a running window of Y position values and to calculate a maximum slope, a minimum slope, and a respective time of said Y position values.

8. A computer readable medium bearing instructions for singulating the limbs of a plurality of animals traversing an instrumented force-sensing floor according to claim 7, wherein the instructions arranged to cause one or more processors upon execution thereof to perform step (c) further comprises an instruction or instructions arranged to increment a counter if the slope of said running window of Y position values is greater than about 2 or less than about −2.

9. A computer readable medium bearing instructions for singulating the limbs of a plurality of animals traversing an instrumented force-sensing floor according to claim 8, wherein the instructions arranged to cause one or more processors upon execution thereof to perform step (c) further comprises an instruction or instructions arranged to increment a positive slope counter by one or to increment a negative slope counter if a slope within said running window exceeds a predetermined minimum rate of change.

10. A computer readable medium bearing instructions for singulating the limbs of a plurality of animals traversing an instrumented force-sensing floor according to claim 9, wherein the instructions arranged to cause one or more processors upon execution thereof to perform step (c) further comprises an instruction or instructions arranged to run a loop wherein the ground reaction force slope is calculated for a second running window having a width less than that of said running window, and wherein a ground reaction force slope counter is incremented by one if the product of two successive ground reaction force slope values are negative.

11. A computer readable medium bearing instructions for singulating the limbs of a plurality of animals traversing an instrumented force-sensing floor according to claim 10, wherein the instructions arranged to cause one or more processors upon execution thereof to perform step (c) further comprises an instruction or instructions arranged to calculate, for a difference in between the start time and the end time is greater than about 30 seconds, average Y position, maximum Y position value, minimum Y position value, maximum ground reaction force, and average ground reaction force.

12. A computer readable medium bearing instructions for singulating the limbs of a plurality of animals traversing an instrumented force-sensing floor according to claim 11, wherein the instructions arranged to cause one or more processors upon execution thereof to perform step (c) further comprises an instruction or instructions arranged to calculate, a maximum slope and a minimum slope within a running window and to store said maximum slope and said minimum slope together with a respective time of occurrence for each of said maximum slope and said minimum slope.

13. A computer readable medium bearing instructions for singulating the limbs of a plurality of animals traversing an instrumented force-sensing floor according to claim 12, wherein the instructions arranged to cause one or more processors upon execution thereof to perform step (c) further comprises an instruction or instructions arranged to assign a number of limbs in a time zone to be one if at least one of the following sets of conditions is satisfied comprising (1) a difference between a maximum and a minimum value of Y position is less than six, a difference between a mean value of Y position and a minimum value of Y position is less than six, said maximum slope is less than five, said minimum slope is greater than negative five, said ground reaction force slope counter is one; (2) said ground reaction force slope counter is one, said maximum slope is greater than or equal to five and the difference in time between said maximum slope and said start time is less than 20 seconds and said minimum slope is greater than negative five; (3) said ground reaction force slope counter is one, said maximum slope is greater than or equal to five, a difference in time between said end time and said time of the maximum slope is less than twenty seconds, and said minimum slope is greater than five; (4) said ground reaction force slope counter is one, said minimum slope is less than or equal to negative five, a difference in time between said end time and said time of the minimum slope is less than twenty seconds, and said maximum slope is less than five; and (5) said ground reaction force slope counter is one, said minimum slope is less than or equal to negative five, a difference in time between said end time and said time of the minimum slope is less than twenty seconds, and said minimum slope is greater than five; and the maximum slope is less than five, (6) said ground reaction force slope counter is one, said minimum slope is less than or equal to negative five, a difference in time between said time of the minimum slope and said start time is less than twenty seconds, and said maximum slope is less than five, and (7) a difference between a maximum value of Y position and the average value of Y position is less than six, a difference between a mean value of Y position and a minimum value of Y position is less than six, said positive slope counter is less than 0.09 times the difference between said start time and said end time, and said negative slope counter is less than 0.09 times a difference between said start time and said end time.

14. A computer readable medium bearing instructions for singulating the limbs of a plurality of animals traversing an instrumented force-sensing floor according to claim 13, wherein the instructions arranged to cause one or more processors upon execution thereof to perform step (c) further comprises an instruction or instructions arranged to assign a number of limbs in a time zone to be three if the following set of conditions is satisfied comprising a difference between a maximum value of Y position and the average value of Y position is greater than six, a difference between a mean value of Y position and a minimum value of Y position is greater than six, said maximum slope is greater than five, said minimum slope is less than negative five, said positive slope counter is greater than 0.09 times the difference between said start time and said end time, and said negative slope counter is greater than 0.09 times a difference between said start time and said end time.

15. A computer readable medium bearing instructions for singulating the limbs of a plurality of animals traversing an instrumented force-sensing floor according to claim 14, wherein the instructions arranged to cause one or more processors upon execution thereof to perform step (c) further comprises an instruction or instructions arranged to assign a number of limbs in a time zone to be two if no set of conditions set forth in claim 13 or claim 14 is satisfied.

16. A computer readable medium bearing instructions for singulating the limbs of a plurality of animals traversing an instrumented force-sensing floor according to claim 15, wherein the instructions arranged to cause one or more processors upon execution thereof to perform step (d) further comprises an instruction or instructions arranged to singulate a single ground reaction force signature for two limbs into two ground reaction force signatures for a single limb.

17. A computer readable medium bearing instructions for singulating the limbs of a plurality of animals traversing an instrumented force-sensing floor according to claim 16, wherein said singulation step further comprises instructions arranged to cause one or more processors upon execution thereof to execute a first loop wherein a running window starts at the tested limb zone starting time and moves toward the limb zone end time to determine if a difference between a Y position at one end of the running window and a Y position at another end of the running window is greater than a predetermined threshold value and recording a y-value at the point at which the first loop is terminated, and to execute a second loop wherein a running window starts at the tested limb zone ending time and moves toward the limb zone start time to determine if a difference between a Y position at one end of the running window and a Y position at another end of the running window is greater than a predetermined threshold value and recording a y-value at the point at which the second loop is terminated.

18. A computer readable medium bearing instructions for singulating the limbs of a plurality of animals traversing an instrumented force-sensing floor according to claim 17, wherein said running window is 5 units wide.

19. A computer readable medium bearing instructions for singulating the limbs of a plurality of animals traversing an instrumented force-sensing floor according to claim 18, wherein said singulation step further comprises instructions arranged to solve, for said single ground reaction force signature for two limbs, two simultaneous equilibrium equations to yield two separate ground force reaction signatures for two singulated limbs.

20. A computer readable medium bearing instructions for singulating the limbs of a plurality of animals traversing an instrumented force-sensing floor according to claim 15, wherein the instructions arranged to cause one or more processors upon execution thereof to perform step (d) further comprises an instruction or instructions arranged to singulate a single ground reaction force signature for three limbs into three ground reaction force signatures for a single limb.

21. A computer readable medium bearing instructions for singulating the limbs of a plurality of animals traversing an instrumented force-sensing floor according to claim 20, wherein said singulation step further comprises instructions arranged to cause one or more processors upon execution thereof to initiate, upon a first time the instructions for singulation are executed, a first loop wherein a running window starts at the tested limb zone starting time plus a threshold of two and moves toward and up to a time at which a minimum Y position slope occurs in the tested limb zone minus a threshold of two, wherein an absolute value of a difference between said running window of two units wide and the Y position vector is evaluated and the loop is broken when said difference is less than two, and wherein a y-value at the point of said first loop termination is stored, and further instructions to execute a second loop wherein a running window starts at the time at which a minimum Y position slope occurs in the tested limb zone minus a threshold of two going backward to the starting time of the limb zone plus a threshold of two, wherein an absolute value of a difference between said running window of two units wide and the Y position vector is evaluated and the loop is terminated when said difference is less than two, and wherein a y-value at the point of said second loop termination is stored.

22. A computer readable medium bearing instructions for singulating the limbs of a plurality of animals traversing an instrumented force-sensing floor according to claim 20, wherein said singulation step further comprises instructions arranged to cause one or more processors upon execution thereof to initiate a first loop wherein a running window starts at the time at which a minimum Y position slope occurs in the tested limb zone plus a threshold of two up to the end time of the limb zone minus a threshold of two, wherein an absolute value of a difference between said running window of two units wide and the Y position vector is evaluated and the loop is terminated when said difference is less than two, and wherein a y-value at the point of said first loop termination is stored, and to initiate a second loop wherein a running window starts at the tested limb zone end time minus a threshold of two units and moves backward to a time at which a minimum Y position slope occurs in the tested limb zone minus a threshold of two units, wherein an absolute value of a difference between said running window of two units wide and the Y position vector is evaluated and the loop is broken when said difference is less than two, and wherein a y-value at the point of said second loop termination is stored.

23. A computer readable medium bearing instructions for singulating the limbs of a plurality of animals traversing an instrumented force-sensing floor according to claim 21 or 22, said singulation step further comprises instructions arranged to solve, for said single ground reaction force signature for three limbs, two simultaneous equilibrium equations to yield two separate ground force reaction signatures for two singulated limbs.

24. A computer readable medium bearing instructions for singulating the limbs of a plurality of animals traversing an instrumented force-sensing floor according to claim 23, said singulation step further comprises instructions arranged to solve, for said single ground reaction force signature for three limbs, at least a plurality of simultaneous equilibrium equations to yield a corresponding plurality of separate ground force reaction signatures for singulated limbs.

25. A computer readable medium bearing instructions for singulating the limbs of a plurality of animals traversing an instrumented force-sensing floor according to claim 1, wherein the instructions arranged to cause one or more processors upon execution thereof to perform step (e) further comprises an instruction or instructions arranged to designate the tested limb as a fore limb if a tested limb zone belongs to a single limb and it is the first limb in the data sequence to be tested and to designate the limb data as indeterminate if the tested limb zone is of a single limb and the average Y position is greater than 72 inches end of the plate or if the tested limb zone is of a single limb and the average Y position is less than 1 inch the front end of the plate.

26. A computer readable medium bearing instructions for singulating the limbs of a plurality of animals traversing an instrumented force-sensing floor according to claim 25, wherein the instructions arranged to cause one or more processors upon execution thereof to perform step (e) further comprises an instruction or instructions arranged to delineate a tested limb as a hind limb if any one of the following sets of conditions is satisfied: (1) the tested limbzone is of a single limb, the limb before the tested limb is fore, the limb before the tested limb is not adjacent an end of the plate, the limb before the tested limb is not adjacent a beginning of the plate, the average ground reaction force of the previous limb is greater than or equal to 1.04 times the average ground reaction force of tested limb and the difference between the average Y Position of the previous and current limb zones is less than five; (2) the tested limbzone is of a single limb, the limb before the tested limb is fore, the difference between the average Y Position of the previous and current limb zones is less than ten; (3) the tested limbzone is of a single limb, the limb before the tested limb is fore, the peak ground reaction force of the previous limb is greater 1.15 times the peak ground reaction force of a current limb; and (4) the tested limbzone is of a single limb, the limb before the tested limb is fore and the ground reaction force slope counter of the current zone is greater than three.

27. A computer readable medium bearing instructions for singulating the limbs of a plurality of animals traversing an instrumented force-sensing floor according to claim 26, wherein the instructions arranged to cause one or more processors upon execution thereof to perform step (e) further comprises an instruction or instructions arranged to designate the limb data as belonging to a fore limb if a tested limb zone belongs to a single limb, the limb before the tested limb is fore, the limb before the tested limb is not adjacent the end of the plate, the limb before the tested limb is not adjacent the beginning of the plate, and a difference between the average Y position of the previous and current limb zones is greater than or equal to five.

28. A computer readable medium bearing instructions for singulating the limbs of a plurality of animals traversing an instrumented force-sensing floor according to claim 26, wherein the instructions arranged to cause one or more processors upon execution thereof to perform step (e) further comprises an instruction or instructions arranged to designate the tested limb as a fore limb if any one of the following sets of conditions is satisfied: (1) the tested limbzone is of a single limb and the limb before the tested limb is hind, the limb before the tested limb is not adjacent the end of the plate, the limb before the tested limb is not adjacent the beginning of the plate, the average ground reaction force of the previous limb is greater than 1.05 times the average ground reaction force of the tested limb, and the difference between the average Y Position of the previous and current limb zones is less than or equal to zero; (2) the tested limbzone is of a single limb, the limb before the tested limb is hind, the average ground reaction force of the previous limb is greater than 1.02 times the average ground reaction force of the current limb and the difference between average Y position of current and previous limbs is less than or equal to −15; (3) the tested limbzone is of a single limb, the limb before the tested limb is hind, the average ground reaction force of the previous limb is greater than 1.1 times the average ground reaction force of current limb; and (4) the tested limbzone is of a single limb, the limb before the tested limb is hind, and the peak ground reaction force of the previous limb is greater than 1.1 the peak ground reaction force of the current limb.

29. A computer readable medium bearing instructions for singulating the limbs of a plurality of animals traversing an instrumented force-sensing floor according to claim 26, wherein the instructions arranged to cause one or more processors upon execution thereof to perform step (e) further comprises an instruction or instructions arranged to designate the tested limb as a hind limb if any one of the following sets of conditions is satisfied: (1) the tested limbzone is of a single limb, the limb before the tested limb is hind, the limb before the tested limb is not adjacent the end of the plate, the limb before the tested limb is not adjacent the beginning of the plate and the average ground reaction force of the previous limb is less than or equal to 1.05 times the average ground reaction force of the tested limb, and the difference between the average Y Position of the previous and current limb zones is greater than zero; (2) the tested limbzone is of a single limb, the limb before the tested limb is hind, and average ground reaction force of the previous limb is greater than or equal to 1.05 times the average ground reaction force of the current limb and the difference between average Y position of current and previous limbs is greater than or equal to forty; (3) the tested limbzone is of a single limb, the limb before the tested limb is hind, and the difference between average Y position of current and previous limbs is greater than or equal to forty.

30. A computer readable medium bearing instructions for singulating the limbs of a plurality of animals traversing an instrumented force-sensing floor according to claim 25, wherein the instructions arranged to cause one or more processors upon execution thereof to perform step (f) further comprises an instruction or instructions arranged to designate a tested limb zone as belonging to a new cow if any one of the following sets of conditions is satisfied: (1) the limb one before current limb is hind, the current limb is fore, the average Y position of the limb before current is greater than the average Y position of the current limb; (2) the limb before the current limb is hind, the current limb is fore, the difference between the start time of the current limb and the end time of the limb before current limb is greater than 0.5 sec; (3) the number of limbs in the tested zone is one, the limb before the current limb is within five inches of the beginning of the plate, and the difference between the average Y position of the limb before the current limb and the average Y position of the current limb is greater than fifteen; (4) the limb before current is hind, the current limb is within about one inch from the front end of the plate, and the average Y position of the limb before the current limb is greater than the average Y position of the current limb.

31. A method for singulating the limbs of a plurality of animals traversing an instrumented force-sensing floor, comprising the steps of:
(a) obtaining a data file comprising positional data and ground reaction force data for said plurality of animals traversing an instrumented force-sensing floor;
(b) dividing the positional data into a plurality of time zones, each time zone having a start time and an end time;
(c) determining whether each of said time zones represents positional data and ground reaction force data for a single limb or for multiple limbs;
(d) singulating multiple limb time zones into a plurality of separate single limb time zones;
(e) identifying each limb in each time zone as a fore limb or a hind limb and a left limb or a right limb;
(f) associating each identified fore and hind limb with a respective one of said plurality of animals.

32. A method for singulating the limbs of a plurality of animals traversing an instrumented force-sensing floor according to claim 31, where step (d) comprises singulating multiple limb time zones via induction into a plurality of separate single limb time zones.

33. A method for singulating the limbs of a plurality of animals traversing an instrumented force-sensing floor according to claim 32, wherein step (a) further comprises obtaining identification data comprising at least one of time data for data recordation, file numbers, animal tag numbers, and animal identification numbers.

34. A method for singulating the limbs of a plurality of animals traversing an instrumented force-sensing floor according to claim 33,
wherein step (a) further comprises calculating a number of animals recorded in each file, and
wherein step (b) further comprises finding a first vector of indices for which a Y-position of a right limb or a left limb is greater than zero, finding a second vector of indices for which a Y-position of a right limb or a left limb is greater than one, and utilizing at least one of said first vector of indices and said second vector of indices to determine said plurality of time zones.

35. A method for singulating the limbs of a plurality of animals traversing an instrumented force-sensing floor according to claim 34, wherein step (c) further comprises determining a maximum and an average ground reaction force between a start time of a tested limb time zone and an end time of a tested limb time zone if the difference between the start time and the end time is greater than about 30 seconds, and storing said maximum and said average ground reaction force.

36. A method for singulating the limbs of a plurality of animals traversing an instrumented force-sensing floor according to claim 35, wherein step (c) further comprises determining said average ground reaction force by calculating a ratio of an impulse variable over a stancetime variable, said impulse variable calculated by applying a multiplier to a ground reaction force curve area defined between said start time of a tested limb time zone and said end time of a tested limb time zone, and said stancetime variable calculated as the difference in time between said start time of a tested limb time zone and said end time of a tested limb time zone.

37. A method for singulating the limbs of a plurality of animals traversing an instrumented force-sensing floor according to claim 36, wherein step (c) further comprises calculating a slope of a running window of Y position values and calculating a maximum slope, a minimum slope, and a respective time of said Y position values.

38. A method for singulating the limbs of a plurality of animals traversing an instrumented force-sensing floor according to claim 37, wherein step (c) further comprises incrementing a counter if the slope of said running window of Y position values is greater than about 2 or less than about −2.

39. A method for singulating the limbs of a plurality of animals traversing an instrumented force-sensing floor according to claim 38, wherein step (c) further comprises incrementing a positive slope counter by one or incrementing a negative slope counter if a slope within said running window exceeds a predetermined minimum rate of change.

40. A method for singulating the limbs of a plurality of animals traversing an instrumented force-sensing floor according to claim 39, wherein step (c) further comprises iteratively calculating a ground reaction force slope for a second running window having a width less than that of said running window, and incrementing a ground reaction force slope counter by one if the product of two successive ground reaction force slope values are negative.

41. A method for singulating the limbs of a plurality of animals traversing an instrumented force-sensing floor according to claim 40, wherein step (c) further comprises calculating, for a difference in between the start time and the end time is greater than about 30 seconds, average Y position, maximum Y position value, minimum Y position value, maximum ground reaction force, and average ground reaction force.

42. A method for singulating the limbs of a plurality of animals traversing an instrumented force-sensing floor according to claim 41, wherein step (c) further comprises calculating a maximum slope and a minimum slope within a running window and to storing said maximum slope and said minimum slope together with a respective time of occurrence for each of said maximum slope and said minimum slope.

43. A method for singulating the limbs of a plurality of animals traversing an instrumented force-sensing floor according to claim 42, wherein step (c) further comprises assigning a number of limbs in a time zone to be one if at least one of the following sets of conditions is satisfied: (1) a difference between a maximum and a minimum value of Y position is less than six, a difference between a mean value of Y position and a minimum value of Y position is less than six, said maximum slope is less than five, said minimum slope is greater than negative five, said ground reaction force slope counter is one; (2) said ground reaction force slope counter is one, said maximum slope is greater than or equal to five and the difference in time between said maximum slope and said start time is less than 20 seconds and said minimum slope is greater than negative five; (3) said ground reaction force slope counter is one, said maximum slope is greater than or equal to five, a difference in time between said end time and said time of the maximum slope is less than twenty seconds, and said minimum slope is greater than five; (4) said ground reaction force slope counter is one, said minimum slope is less than or equal to negative five, a difference in time between said end time and said time of the minimum slope is less than twenty seconds, and said maximum slope is less than five; and (5) said ground reaction force slope counter is one, said minimum slope is less than or equal to negative five, a difference in time between said end time and said time of the minimum slope is less than twenty seconds, and said minimum slope is greater than five; and the maximum slope is less than five, (6) said ground reaction force slope counter is one, said minimum slope is less than or equal to negative five, a difference in time between said time of the minimum slope and said start time is less than twenty seconds, and said maximum slope is less than five, and (7) a difference between a maximum value of Y position and the average value of Y position is less than six, a difference between a mean value of Y position and a minimum value of Y position is less than six, said positive slope counter is less than 0.09 times the difference between said start time and said end time, and said negative slope counter is less than 0.09 times a difference between said start time and said end time.

44. A method for singulating the limbs of a plurality of animals traversing an instrumented force-sensing floor according to claim 43, wherein step (c) further comprises assigning a number of limbs in a time zone to be three if a difference between a maximum value of Y position and the average value of Y position is greater than six, a difference between a mean value of Y position and a minimum value of Y position is greater than six, said maximum slope is greater than five, said minimum slope is less than negative five, said positive slope counter is greater than 0.09 times the difference between said start time and said end time, and said negative slope counter is greater than 0.09 times a difference between said start time and said end time.

45. A method for singulating the limbs of a plurality of animals traversing an instrumented force-sensing floor according to claim 44, wherein step (c) further comprises assigning a number of limbs in a time zone to be two if no set of conditions is satisfied.

46. A method for singulating the limbs of a plurality of animals traversing an instrumented force-sensing floor according to claim 45, wherein step (d) further comprises singulating a single ground reaction force signature for two limbs into two ground reaction force signatures for a single limb.

47. A method for singulating the limbs of a plurality of animals traversing an instrumented force-sensing floor according to claim 46, wherein said singulation step further comprises performing a first iterative calculation using a running window starting at the tested limb zone starting time and moving toward the limb zone end time to determine if a difference between a Y position at one end of the running window and a Y position at another end of the running window is greater than a predetermined threshold value and recording a y-value at the point at which the first interative calculation is terminated, and performing a second iterative calculation using a running window starting at the tested limb zone ending time and moving toward the limb zone start time to determine if a difference between a Y position at one end of the running window and a Y position at another end of the running window is greater than a predetermined threshold value and recording a y-value at the point at which the second iterative calculation is terminated.

48. A method for singulating the limbs of a plurality of animals traversing an instrumented force-sensing floor according to claim 46, wherein said running window is 5 units wide.

49. A method for singulating the limbs of a plurality of animals traversing an instrumented force-sensing floor according to claim 47, wherein said singulation step further comprises solving, for said single ground reaction force signature for two limbs, two simultaneous equilibrium equations to yield two separate ground force reaction signatures for two singulated limbs.

50. A method for singulating the limbs of a plurality of animals traversing an instrumented force-sensing floor according to claim 49, wherein step (d) further comprises singulation of a single ground reaction force signature for three limbs into three ground reaction force signatures for a single limb.

51. A method for singulating the limbs of a plurality of animals traversing an instrumented force-sensing floor according to claim 50, wherein said singulation step further comprises, upon a first instance of singulation, performing a first iterative calculation using a running window starting at the tested limb zone starting time plus a threshold of two and moving toward and up to a time at which a minimum Y position slope occurs in the tested limb zone minus a threshold of two, calculating an absolute value of a difference between said running window of two units wide and the Y position vector, and terminating said iterative calculation when said difference is less than two, and storing a y-value at the point of said termination of said iterative calculation, and performing a second iterative calculation using a running window starting at the time at which a minimum Y position slope occurs in the tested limb zone minus a threshold of two going backward to the starting time of the limb zone plus a threshold of two, calculating an absolute value of a difference between said running window of two units wide and the Y position vector is evaluated, terminating said second iterative calculation when said difference is less than two, and storing a y-value at the point at which said second iterative calculation is terminated.

52. A method for singulating the limbs of a plurality of animals traversing an instrumented force-sensing floor according to claim 50, wherein said singulation step further comprises initiating a first iterative calculation using a running window starting at the time at which a minimum Y position slope occurs in the tested limb zone plus a threshold of two up to the end time of the limb zone minus a threshold of two, calculating an absolute value of a difference between said running window of two units wide and the Y position vector, terminating said first iterative calculation when said difference is less than two, storing a y-value at the point of said first iterative calculation termination, initiating a second iterative calculation using a running window starting at the tested limb zone end time minus a threshold of two units and moving backward to a time at which a minimum Y position slope occurs in the tested limb zone minus a threshold of two units, calculating an absolute value of a difference between said running window of two units wide and the Y position vector, terminating the second iterative calculation when said difference is less than two, and storing a y-value at the point of said second iterative calculation termination.

53. A method for singulating the limbs of a plurality of animals traversing an instrumented force-sensing floor according to claim 51 or 52, said singulation step further comprising solving, for said single ground reaction force signature for three limbs, two simultaneous equilibrium equations to yield two separate ground force reaction signatures for two singulated limbs.

54. A method for singulating the limbs of a plurality of animals traversing an instrumented force-sensing floor according to claim 53, said singulation step further comprising solving, for said single ground reaction force signature for three limbs, at least a plurality of simultaneous equilibrium equations to yield a corresponding plurality of separate ground force reaction signatures for singulated limbs.

55. A computer readable medium bearing instructions for singulating the limbs of a plurality of animals traversing an instrumented force-sensing floor according to claim 31, wherein the step (e) further comprises designating the tested limb as a fore limb if a tested limb zone belongs to a single limb and it is the first limb in the data sequence to be tested and to designate the limb data as indeterminate if the tested limb zone is of a single limb and the average Y position is greater than 72 inches end of the plate or if the tested limb zone is of a single limb and the average Y position is less than 1 inch the front end of the plate.

56. A method for singulating the limbs of a plurality of animals traversing an instrumented force-sensing floor according to claim 55, wherein step (e) further comprises delineating a tested limb as a hind limb if any one of the following sets of conditions is satisfied: (1) the tested limbzone is of a single limb, the limb before the tested limb is fore, the limb before the tested limb is not adjacent an end of the plate, the limb before the tested limb is not adjacent a beginning of the plate, the average ground reaction force of the previous limb is greater than or equal to 1.04 times the average ground reaction force of tested limb and the difference between the average Y Position of the previous and current limb zones is less than five; (2) the tested limbzone is of a single limb, the limb before the tested limb is fore, the difference between the average Y Position of the previous and current limb zones is less than ten; (3) the tested limbzone is of a single limb, the limb before the tested limb is fore, the peak ground reaction force of the previous limb is greater 1.15 times the peak ground reaction force of a current limb, and (4) the tested limbzone is of a single limb, the limb before the tested limb is fore and the ground reaction force slope counter of the current zone is greater than three.

57. A method for singulating the limbs of a plurality of animals traversing an instrumented force-sensing floor according to claim 56, wherein step (e) further comprises designating the limb data as belonging to a fore limb if a tested limb zone belongs to a single limb, the limb before the tested limb is fore, the limb before the tested limb is not adjacent the end of the plate, the limb before the tested limb is not adjacent the beginning of the plate, and a difference between the average Y position of the previous and current limb zones is greater than or equal to five.

58. A method for singulating the limbs of a plurality of animals traversing an instrumented force-sensing floor according to claim 56, wherein step (e) further comprises designating the tested limb as a fore limb if any one of the following sets of conditions is satisfied: (1) the tested limbzone is of a single limb and the limb before the tested limb is hind, the limb before the tested limb is not adjacent the end of the plate, the limb before the tested limb is not adjacent the beginning of the plate, the average ground reaction force of the previous limb is greater than 1.05 times the average ground reaction force of the tested limb, and the difference between the average Y Position of the previous and current limb zones is less than or equal to zero; (2) the tested limbzone is of a single limb, the limb before the tested limb is hind, the average ground reaction force of the previous limb is greater than 1.02 times the average ground reaction force of the current limb and the difference between average Y position of current and previous limbs is less than or equal to −15; (3) the tested limbzone is of a single limb, the limb before the tested limb is hind, the average ground reaction force of the previous limb is greater than 1.1 times the average ground reaction force of current limb; and (4) the tested limbzone is of a single limb, the limb before the tested limb is hind, and the peak ground reaction force of the previous limb is greater than 1.1 the peak ground reaction force of the current limb.

59. A method for singulating the limbs of a plurality of animals traversing an instrumented force-sensing floor according to claim 56, wherein step (e) further comprises designating the tested limb as a hind limb if any one of the following sets of conditions is satisfied: (1) the tested limbzone is of a single limb, the limb before the tested limb is hind, the limb before the tested limb is not adjacent the end of the plate, the limb before the tested limb is not adjacent the beginning of the plate and the average ground reaction force of the previous limb is less than or equal to 1.05 times the average ground reaction force of the tested limb, and the difference between the average Y Position of the previous and current limb zones is greater than zero; (2) the tested limbzone is of a single limb, the limb before the tested limb is hind, and average ground reaction force of the previous limb is greater than or equal to 1.05 times the average ground reaction force of the current limb and the difference between average Y position of current and previous limbs is greater than or equal to forty; (3) the tested limbzone is of a single limb, the limb before the tested limb is hind, and the difference between average Y position of current and previous limbs is greater than or equal to forty.

60. A method for singulating the limbs of a plurality of animals traversing an instrumented force-sensing floor according to claim 55, wherein step (f) further comprises designating a tested limb zone as belonging to a new cow if any one of the following sets of conditions is satisfied: (1) the limb one before current limb is hind, the current limb is fore, the average Y position of the limb before current is greater than the average Y position of the current limb; (2) the limb before the current limb is hind, the current limb is fore, the difference between the start time of the current limb and the end time of the limb before current limb is greater than 0.5 sec; (3) the number of limbs in the tested zone is one, the limb before the current limb is within five inches of the beginning of the plate, and the difference between the average Y position of the limb before the current limb and the average Y position of the current limb is greater than fifteen; (4) the limb before current is hind, the current limb is within about one inch from the front end of the plate, and the average Y position of the limb before the current limb is greater than the average Y position of the current limb.

* * * * *